(12) United States Patent
Chevillet et al.

(10) Patent No.: US 11,301,044 B1
(45) Date of Patent: Apr. 12, 2022

(54) WEARABLE BRAIN COMPUTER INTERFACE

(71) Applicant: Meta Platforms, Inc., Menlo Park, CA (US)

(72) Inventors: Mark Allan Chevillet, Redwood City, CA (US); Patrick Mineault, San Francisco, CA (US); Emily Mittag Mugler, Redwood City, CA (US); Soo Yeon Kim Jennings, Sunnyvale, CA (US)

(73) Assignee: Meta Platforms, Inc., Menlo Park, CA (US)

( * ) Notice: Subject to any disclaimer, the term of this patent is extended or adjusted under 35 U.S.C. 154(b) by 81 days.

(21) Appl. No.: 16/773,057

(22) Filed: Jan. 27, 2020

Related U.S. Application Data

(60) Provisional application No. 62/797,578, filed on Jan. 28, 2019.

(51) Int. Cl.
| | |
|---|---|
| *G06F 3/01* | (2006.01) |
| *H01S 5/183* | (2006.01) |
| *H01S 5/42* | (2006.01) |
| *H01S 5/00* | (2006.01) |
| *A61B 5/366* | (2021.01) |
| *A61B 5/374* | (2021.01) |
| *A61B 1/00* | (2006.01) |
| *A61B 6/03* | (2006.01) |

(52) U.S. Cl.
CPC .......... *G06F 3/015* (2013.01); *A61B 1/00172* (2013.01); *A61B 5/366* (2021.01); *A61B 5/374* (2021.01); *A61B 6/03* (2013.01); *H01S 5/005* (2013.01); *H01S 5/18311* (2013.01); *H01S 5/423* (2013.01)

(58) Field of Classification Search
CPC .......... G06F 3/015; A61B 5/375; A61B 5/366; H01S 5/423; H01S 5/18311; H01S 5/005
See application file for complete search history.

(56) References Cited

U.S. PATENT DOCUMENTS

| | | |
|---|---|---|
| 7,139,600 B2 | 11/2006 | Maki et al. |
| 8,718,777 B2 | 5/2014 | Lowry et al. |
| 9,114,226 B1 | 8/2015 | Lash et al. |

(Continued)

OTHER PUBLICATIONS

United States Office Action, U.S. Appl. No. 16/544,305, dated Jul. 28, 2020, 14 pages.

(Continued)

*Primary Examiner* — Liliana Cerullo
(74) *Attorney, Agent, or Firm* — Fenwick & West LLP

(57) ABSTRACT

Embodiments relate to a brain computer interface (BCI) including a light source subsystem, an interface transmitting light from the light source subsystem to a body region of a user, and a detector subsystem coupled to the interface and configured to receive light signals from the body region of the user. The light source subsystem, the interface, and the detector subsystem are coupled to other electronics providing power, computing functionality, and/or other functionality. The BCI is designed to be worn at a head region of a user and to generate optical signals that can be used to characterize brain activity of the user, where decoded brain activity can be used as inputs to control other systems and/or electronic content provided to the user.

19 Claims, 29 Drawing Sheets

(56) References Cited

U.S. PATENT DOCUMENTS

| | | | |
|---|---|---|---|
| 9,864,190 B2 | 1/2018 | Mandella et al. | |
| 2009/0088649 A1 | 4/2009 | Ninomiya et al. | |
| 2010/0210911 A1 | 8/2010 | Shimotsu | |
| 2012/0189244 A1 | 7/2012 | Bowen et al. | |
| 2015/0338917 A1 | 11/2015 | Steiner et al. | |
| 2015/0374255 A1 | 12/2015 | Vasapollo | |
| 2016/0239084 A1 | 8/2016 | Connor | |
| 2017/0231501 A1* | 8/2017 | Culver | A61B 5/742 |
| | | | 600/425 |
| 2019/0107888 A1 | 4/2019 | Sereshkeh et al. | |
| 2020/0038653 A1 | 2/2020 | Sitaram et al. | |
| 2020/0089321 A1 | 3/2020 | Kacelenga | |
| 2020/0187841 A1* | 6/2020 | Ayyad | A61B 5/377 |
| 2020/0337653 A1 | 10/2020 | Alcaide et al. | |
| 2020/0352487 A1* | 11/2020 | Ray | A61B 5/1075 |

OTHER PUBLICATIONS

Non-Final Office Action dated Aug. 12, 2021 for U.S. Appl. No. 16/773,036, filed Jan. 27, 2020, 18 pages.

\* cited by examiner

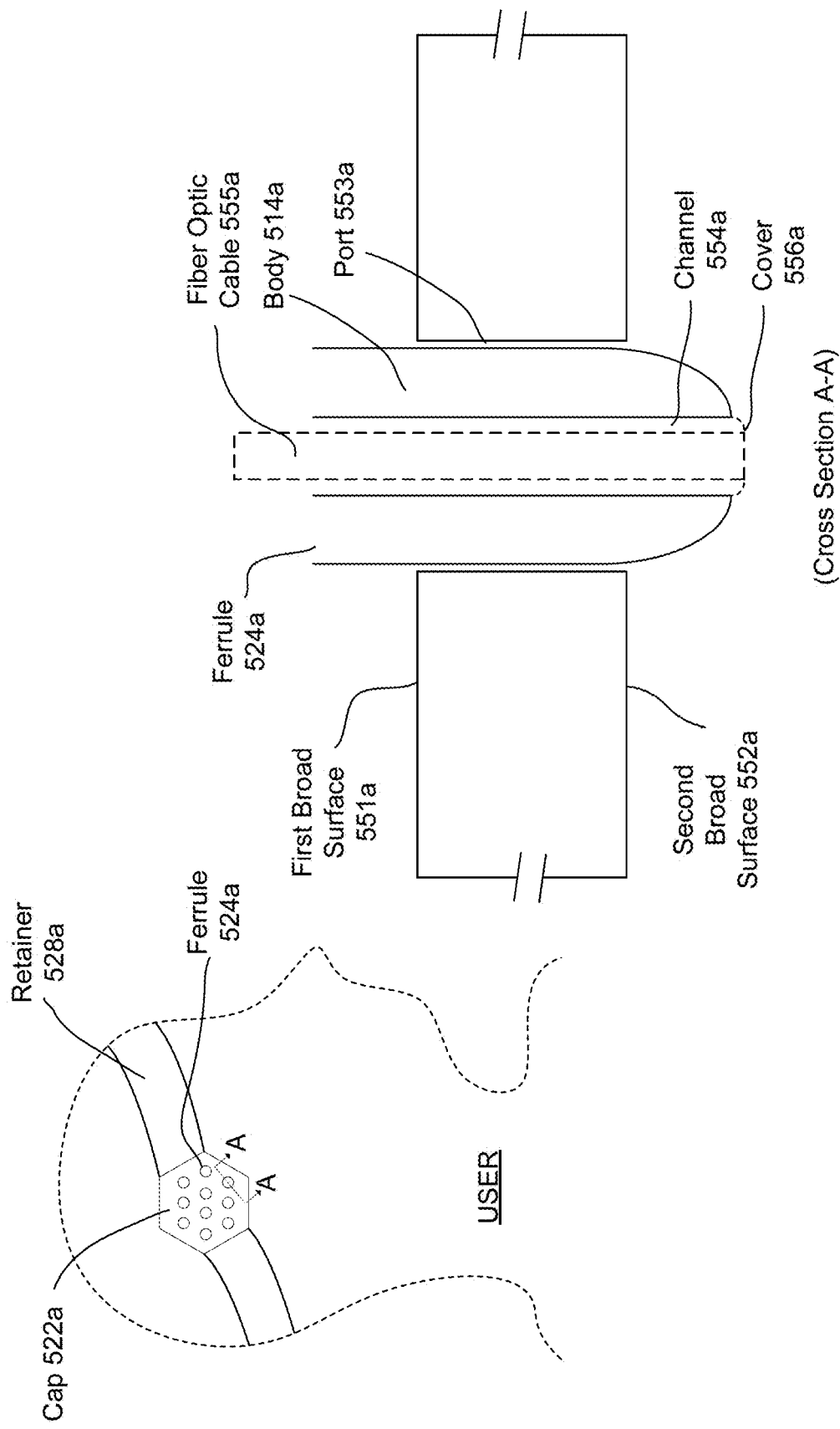

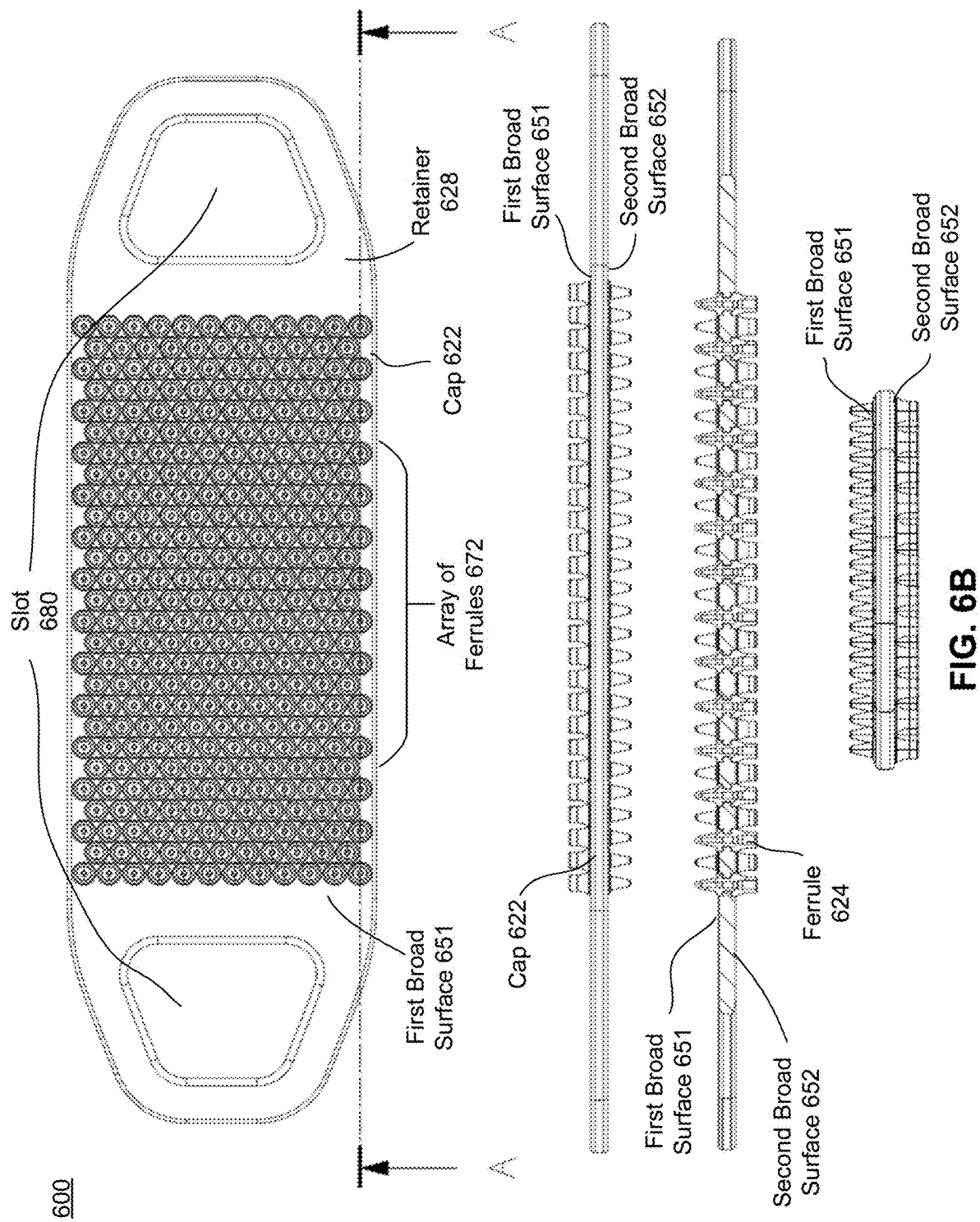

WEARABLE BRAIN COMPUTER INTERFACE

CROSS REFERENCE TO RELATED APPLICATIONS

This application claims the benefit of U.S. Provisional Application No. 62/797,578, filed Jan. 28, 2019, which is incorporated by reference in its entirety.

BACKGROUND

This disclosure relates generally to brain computer interface systems, and specifically to a wearable brain computer interface system with an increased dynamic range sensor.

Communication via physical actions, such as textual entry or manipulation of a user interface on a mobile or other device is a key form of interaction amongst individuals today. Additionally, certain online systems, such as online social networks, thrive on the network of users that frequent the online social network on a consistent basis. One component of online social networks is the ability of a user to interact with objects (e.g., electronically provided content) in an online or virtual setting. In many scenarios, detection of interactions requires the user to type or enter words and phrases through a physical means (e.g., a keyboard or clicking on a virtual keyboard) and/or to audibly provide commands. Physically entering words and phrases or providing audible commands may be cumbersome or impossible for certain individuals. Additionally, and more generally, physical entry of words and phrases for all individuals is often an inefficient way to communicate, as typing or otherwise manipulating various user interfaces can be cumbersome.

Brain computer interface (BCI) systems are being explored in relation to some of these problems. However, traditional brain computer interface (BCI) systems typically implement electrical signal detection methods to characterize brain activity. Such systems are typically used in clinical or academic settings, and often are not designed for use by users during their normal daily lives. In relation to user factors, such systems often lack features that allow users to properly position sensing components in a repeatable and reliable manner, as well as to maintain contacts between sensing components and desired body regions as a user moves throughout his or her daily life. Miniaturization of such BCI systems also provides challenges.

Additionally, fields exploring other sensing regimes for detection and decoding of brain activity are nascent, and traditional sensors used for other sensing regimes have insufficient dynamic range and often provide limitations in readout speed, thereby limiting their use in applications where rapid decoding of brain activity is important.

SUMMARY

Disclosed herein are systems and methods for enabling a user to communicate using a brain computer interface (BCI) system through unspoken communications. As used hereafter, unspoken methods and/or unspoken communications refer to communications that can be performed by an individual through non-verbal (e.g., without verbal sounds), non-physical (e.g., not inputted by an individual through a physical means such as a keyboard, mouse, touchscreen, and the like), and/or non-expressive (e.g., not expressed through facial features, body language, and the like) means.

Generally, a BCI system interprets an individual's brain activity to characterize intentions of the individual in interacting with content in the environment of the user. In particular embodiments, the BCI system includes a light source subsystem, a detector subsystem, and an interface including optical fibers coupled to the light source subsystem and/or detector subsystem, and to a body region of a user. The light source subsystem, the interface, and the detector subsystem are coupled to other electronics providing power and/or computing functionality. The BCI system components are also configured in a wearable form factor that allows a user to repeatably and reliably position light transmitting and light sensing components at the body region. As such, the system can include components appropriate for a small form factor that is portable and worn discreetly at a head region of the user.

Embodiments also relate to a sensor system for a brain computer interface (BCI) that enables detection and decoding of brain activity by optical tomography. The sensor system includes an array of pixels arranged as grouped pixel units to provide increased dynamic range. One or more of the grouped pixel units can operate in a saturated mode while providing information useful for decoding brain activity. Furthermore, the grouped pixel units are arranged to enable fast readout by a pixel scanner, thereby increasing detection and decoding ability by systems implementing the sensor design. The grouped pixel units of the sensor system are aligned with optical fibers of an interface to a body region of a user, where the optical fibers can be retained in position relative to the grouped pixel units by an optically transparent substrate that provides mechanical support while minimizing factors associated with divergence of light transmitted through optical fibers.

Embodiments also relate to a brain computer interface system that includes a retainer and cap assembly for transmitting light to a user's head region and transmitting optical signals from the user's head region to a detector subsystem. The retainer is configured to secure the cap assembly to a head region of a user. The cap assembly includes an array of ports that retain an array of ferrules. A first ferrule in the array of ferrules can include a channel that extends at least partially through the body of the ferrule. The channel retains a fiber optic cable such that the fiber optic cable is in communication with a head region of a user during a mode of operation. The cap includes an elastic portion such that, in a mode of operation, the cap and array of ferrules are biased towards the head region of a user.

Embodiments also relate to decoding architecture that rapidly (e.g., in real time or near real time) decodes light-derived signals to extract predicted user actions or intents (e.g., commands) in relation to interactions with objects (e.g., virtual objects, physical objects), such that the user can manipulate the objects or otherwise receive assistance without manually interacting with an input device (e.g., touch input device, audio input device, etc.). The decoding architecture thus enables a neural decoding process with a neural signal stream as an input, and provides feedback to the user, where the feedback is used to train the neural decoding algorithm and user behavior. The neural signals can be blood oxygenation level dependent (BOLD) signals associated with activation of different articulators of the motor cortex, and signals can characterize both actual and imagined motor cortex-related behaviors. With training of the decoding algorithm, rapid calibration of the BCI for new users can additionally be achieved.

BRIEF DESCRIPTION OF THE DRAWINGS

FIG. 5A depicts a schematic and cross sectional view of an embodiment of an interface to a head region of a user, according to an embodiment.

FIG. 6B depicts a top, side, cross sectional, and front view of the embodiment of a cap shown in FIG. 6A.

Figure 1A:
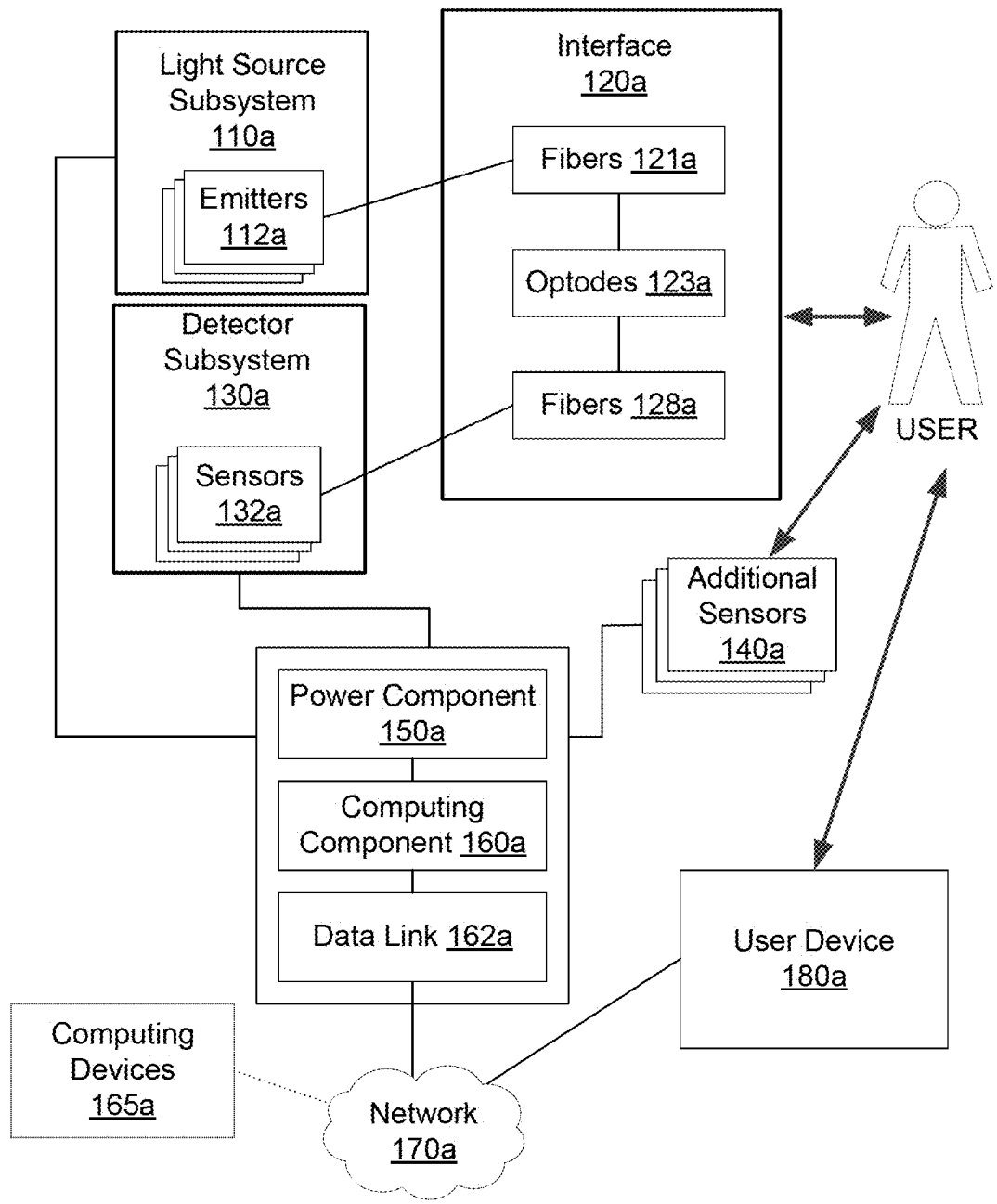
FIG. 1A is a block diagram of a BCI system for detecting and decoding brain activity of a user, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

It is noted that wherever practicable similar or like reference numbers may be used in the figures and may indicate similar or like functionality. For example, a letter after a reference numeral, such as "150a," indicates that the text refers specifically to the element having that particular reference numeral. A reference numeral in the text without a following letter, such as "150," refers to any or all of the elements in the figures bearing that reference numeral (e.g. "computing component 150" in the text refers to reference numerals "computing component 150a" and/or "computing component 150b" in the figures).

DETAILED DESCRIPTION

1. Overview

Embodiments relate to a brain computer interface (BCI) including a light source subsystem, an interface transmitting light from the light source subsystem to a body region of a user, and a detector subsystem coupled to the interface and configured to receive light signals from the body region of the user. The light source subsystem, the interface, and the detector subsystem are coupled to other electronics providing power and/or computing functionality. The BCI is designed to be worn at a head region of a user and to generate optical signals that can be used to characterize brain activity of the user, where decoded brain activity can be used as inputs to control other systems and/or electronic content provided to the user.

In relation to brain activity sensing, embodiments also relate to a light source subsystem of the BCI, where the light source subsystem is provided in a miniaturized form factor that outputs light with appropriate characteristics to enable measurement of blood oxygenation by the detector subsystem, where oxygenation levels can be determined relative to a reference state. In some embodiments, the detector subsystem is configured to measure other types of optical brain signals. The light source subsystem also includes individually addressable light emitters that cooperate with readout operations of a pixel scanner associated with the detector subsystem.

In relation to wearability, embodiments also relate to a wearable component that interfaces the light source subsystem and other system components to the head region of the user during use, in order to assess brain activity in a portable manner. The wearable component includes aspects that reliably bias optodes coupled to the light source subsystem and/or the detector subsystem to the user's head as the user moves about in his or her daily life.

In relation to brain activity sensing and generation of outputs for optical tomography, embodiments also relate to a detector subsystem that can be included with the BCI, where the sensor system enables detection and decoding of brain activity by optical tomography. In some embodiments, detection methodologies other than optical tomography may be used by the detector subsystem. The sensor system includes an array of pixels arranged as grouped pixel units to provide increased dynamic range. One or more of the grouped pixel units can operate in a saturated mode while providing information useful for decoding brain activity. Furthermore, the grouped pixel units are arranged to enable fast readout by a pixel scanner (e.g., line scanner), thereby increasing detection and decoding ability by systems implementing the sensor design. The grouped pixel units of the sensor system are aligned with optical fibers of an interface to a body region of a user, where the optical fibers can be retained in position relative to the grouped pixel units by an optically transparent substrate that provides mechanical support while minimizing factors associated with divergence of light transmitted through optical fibers.

2. System Environment

Figure 1B:
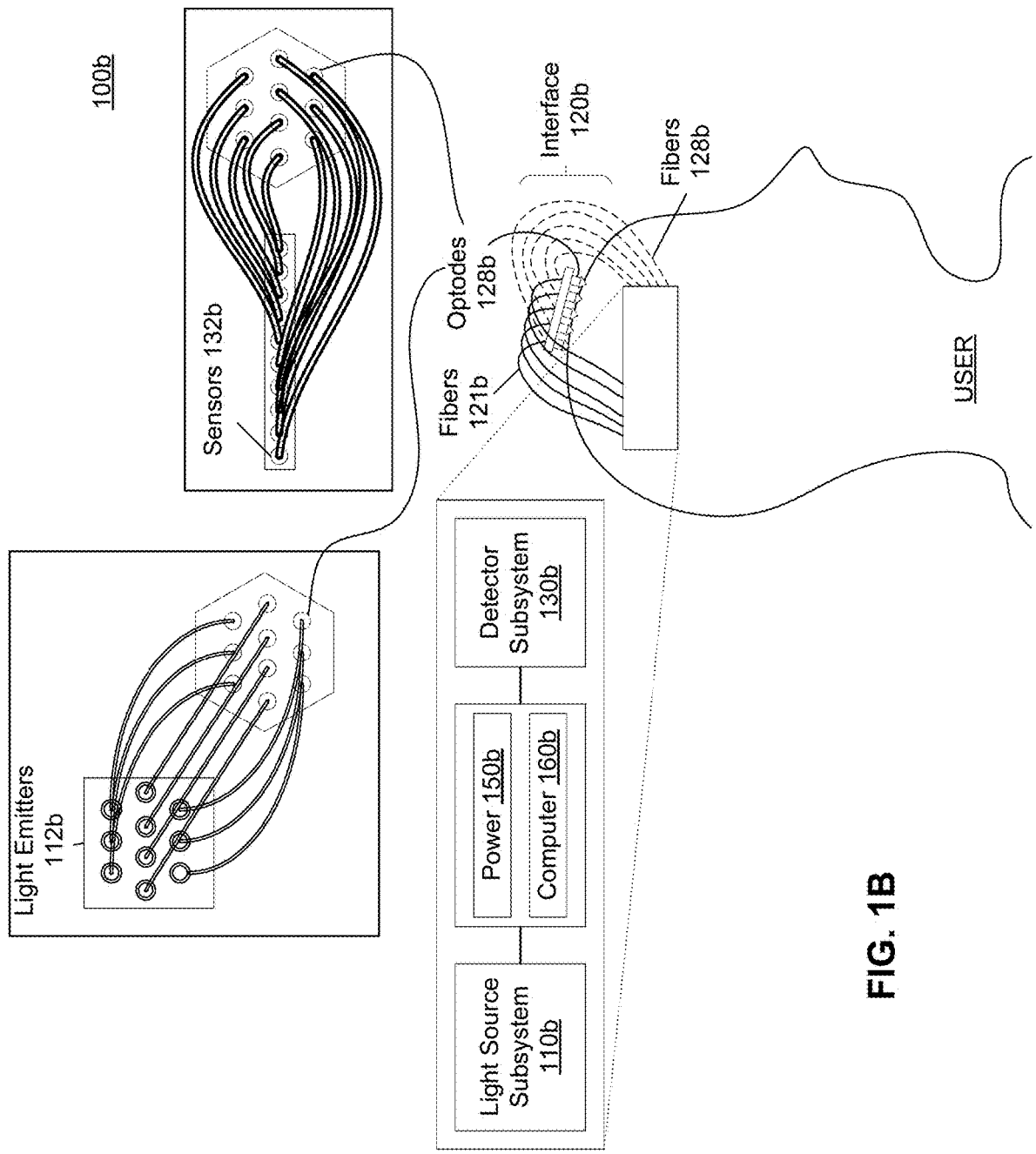
FIG. 1B is a schematic of an embodiment of the BCI system shown in FIG. 1A.

FIG. 1A is a block diagram of a system 100a (e.g., a BCI system) for detecting and decoding brain activity of a user, in accordance with one or more embodiments. FIG. 1B is a schematic of an embodiment of the BCI system 100b shown in FIG. 1A. The system 100 includes a light source subsystem 110, an interface 120 transmitting light from the light source subsystem 110 to a head region of a user, and a detector subsystem 130 coupled to the interface 120 and configured to receive light signals from the head region of the user. The light source subsystem 110, the detector subsystem 130, and/or additional sensors 140 can be coupled to a power component 150 and a computing component 160, which processes and decodes neural stream signals for delivery of feedback to a user device 180 through a network 170.

As described in relation to other system components above and below, the housing 105a can house one or more of: the light source subsystem 110a, the detector subsystem 132a, the power component 150a, the computing component 160a, a data link 162a, and additional sensors 140a. The housing 105a can also house at least a portion of the interface 120a that is head-mountable for positioning signal transmission components at the head region of a user. The housing 105a can be head-mounted or can be coupled to the user in another manner. The housing can be composed of a polymer material and/or any other suitable materials.

The system 100 is thus designed to be worn by a user during use. Emitters 112 of the light source subsystem 110 and sensors 132 of the detector subsystem 130 can be positioned and retained at the head region of the user through the interface 120, through use of optical fibers 121 and 128 and optodes 123 the maintain positions of terminal regions of the optical fibers at the head region of the user. The interface 120, with optodes 123, is configured to enable characterization of brain activity from one or more regions of the user's brain through a non-invasive method. Specifically, the one or more emitters 112 emit light and the one or more sensors 132 capture signals from the head region of the user, based on the emitted light. In some embodiments, the interface 120 is designed to fully cover the head of the user. In other embodiments, the interface 120 is designed to cover a portion of the head, depending on the region(s) of interest associated with applications for decoding brain activity.

In various embodiments, the emitters 112 and sensors 132 enable optical tomography methods for receiving neural signals from the user, where the signals can be subsequently decoded and used for other applications (e.g., as control inputs that allow the user to control behavior of devices in his or her environment). The emitters 112 can emit a signal that is absorbed and/or attenuated by neurons or networks of neurons in the region of the brain, and/or cause a physiological response that can be measured. The sensors 132 detect a signal (e.g., backscattered light) from the same region of the brain. In one embodiment, the signal emitted by the emitters 112 and captured by the sensors 132 is light in the visible spectrum. Additionally or alternatively, in other embodiments, the signal emitted by the emitters 112 and captured by the sensors 132 is light in the non-visible spectrum.

The light source subsystem 110 is in communication with a power component 150 that enables the emitters 112 to transmit light. The light source subsystem 110 can also be in communication with a computing component 160 of system electronics. For example, the light source subsystem 110 can receive inputs from the computing component 160 and can provide inputs to the emitters 112 to coordinate light transmission from the emitters 112 (e.g., in relation to operation of the detector subsystem 130 in coordination with the light source subsystem 110). More specifically, the light source subsystem 110 receives instructions for transitioning the emitters between operation states (e.g., on states, off states) and/or within variations of operation states (e.g., a high power mode in the on state, a low power mode in the on state, etc.). The light source subsystem and the emitters 112 are described in more detail below.

The detector subsystem 130 receives the detected signals from the sensors 132, through coupling of the sensors 132 to the interface 120 to the user. The detector subsystem 130 can also be in communication with the power component to enable sensing, signal pre-processing, and/or signal transmission functions of the detector subsystem 130. The detector subsystem 130 can also be in communication with the computing component 160 of system electronics, in order to support detection operation modes (e.g., sensor scanning modes) and/or other operation modes (e.g., signal transmission modes) of the detector subsystem 130. In relation to the sensors 132 of the detector subsystem 130, the sensors 132 can include complementary metal oxide semiconductor (CMOS) architecture and/or another architecture, as described in more detail below.

The system 100 can additionally include other sensors 140 for detecting user behavior. The additional sensors 140 can also be coupled to the power component 150 and/or the computing component 160 and provide signals useful for decoding brain activity of the user, as described in more detail below.

While the computing component 160 of the system can be implemented onboard the wearable components of the system 100, the computing component 160 can additionally or alternatively be supported by or in communication with other computing devices 165 and/or user a user device 180, for instance, through the network 170. Examples of computing devices 165 and/or user devices 180 include a personal computer (PC), a desktop computer, a laptop computer, a notebook, a tablet PC executing an operating system, for example, a Microsoft Windows-compatible operating system (OS), Apple OS X, and/or a Linux distribution. In other embodiments, the computing devices and/or user devices can be any device having computer functionality, such as a personal digital assistant (PDA), mobile telephone, smartphone, wearable computing device, or any other suitable computing device. The computing component 160 and/or other computing devices can execute instructions (e.g., computer code) stored on a computer-readable storage medium in order to perform the steps and processes described herein for enabling unspoken communications for control of other systems by a user. Collectively, the computing component 160 and any other computing devices, with the network 170, can operate as a computing system for implementation of methods according to specific applications of use of the system 100.

Generally, the computing system determines intentions of the user from signals provided by the detector subsystem 130, where the intentions describe user wishes in relation to interacting with electronic content or a virtual assistant. The computing system can determine the intentions that correspond to the neural signals that were gathered by the detector subsystem 130 by applying a predictive model that is trained to predict intentions from neural activity. The computing system can train the predictive model using training data including gathered experimental datasets corresponding to neural activity of previously observed individuals. Intentions can be decoded into communication related components (e.g., phonemes, words, phrases, sentences, etc.). In some related embodiments, the computing system can enable a user to access an online social networking system, and therefore, allows users to communicate with one another through the online social networking system. As such, the computing system may communicate on behalf of the individual through the network 170 with other computing devices (e.g., computing device 165, user device 180) of the social networking system. In some embodiments, the computing system can communicate on behalf of the individual to other computing devices using the predicted phonemes, words, phrases, and/or sentences.

The network 170 facilitates communications between the one or more computing devices. The network 170 may be any wired or wireless local area network (LAN) and/or wide area network (WAN), such as an intranet, an extranet, or the Internet. In various embodiments, the network 170 uses standard communication technologies and/or protocols. Examples of technologies used by the network 170 include Ethernet, 802.11, 3G, 4G, 802.16, or any other suitable communication technology. The network 170 may use wireless, wired, or a combination of wireless and wired communication technologies. Examples of protocols used by the network 170 include transmission control protocol/Internet protocol (TCP/IP), hypertext transport protocol (HTTP), simple mail transfer protocol (SMTP), file transfer protocol (TCP), or any other suitable communication protocol.

3. System—Neuroimaging Modalities

The system 100 described above operates to enable optical tomography or optical topography-associated modalities for decoding neural activity. The system 100 can characterize blood/tissue characteristics of the user through diffuse optical tomography/topography (DOT) modalities, in relation to characterizing cerebral blood flow, cerebral blood oxygenation, and/or other features indicative of brain activity. The system 100 can additionally or alternatively support other optical tomography or near-infrared spectroscopy approaches, including one or more of: functional near-infrared spectroscopy (fNIRS), functional time-domain near-infrared spectroscopy (TD-fNIRS), diffuse correlation spectroscopy (DC S), speckle contrast optical tomography (SCOT), time-domain interferometric near-infrared spectroscopy (TD-iNIRS), hyperspectral imaging, polarization-sensitive speckle tomography (PSST), spectral decorrelation, auto-fluorescence tomography, and photoacoustic imaging.

4. System Components 4.1 System—Light Sources

Figure 2:
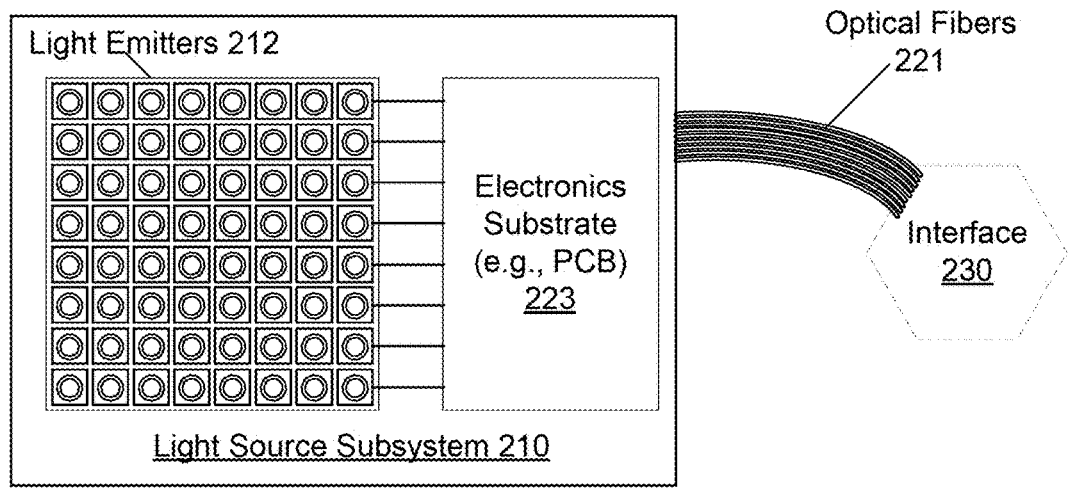
FIG. 2 depicts schematics of portions of a light source subsystem, in accordance with one or more embodiments.

FIG. 2 depicts a schematic of a light source subsystem 210, in accordance with one or more embodiments. The light source subsystem 210 includes one or more emitters 212. The emitter(s) 212 function to emit light having suitable parameters, where the light interacts with a region of interest (e.g., the head region of the user), and is subsequently transmitted to a detector subsystem (described below) for characterization of the region of interest.

The light source subsystem 210 includes laser light emission elements but can include light emitting diode (LED) elements or other types of light emitters in alternative embodiments. In relation to laser light emission elements, the light source subsystem 210 can include vertical cavity surface emitting laser (VCSEL) elements with semiconductor architecture for perpendicular beam emission. Use of VCSEL elements contributes to a compact light emission configuration that provides suitable power for wearable applications requiring high power light output for optical detection of characteristics of a multidimensional region of interest (e.g., a head region of a user). In relation to laser light emission elements, the light source subsystem 210 can alternatively include emitters with conventional semiconductor architecture for edge beam emission from surfaces cleaved from a semiconductor wafer.

Emitters 212 of the light source subsystem 210 include emitters configured to emit light in the visible spectrum and emitters configured to emit light in the non-visible spectrum. For BCI applications involving characterization of brain activity, the emitters include emitters configured to emit red wavelength light and near-infrared light. However, in alternative variations, the emitters 212 can be configured to emit only a single wavelength of light, or other wavelengths of light.

Each emitter of the light source subsystem 210 has its own die physically coupled to an electronics substrate 223 (e.g., printed circuit board) of system electronics, such that each emitter of the light source subsystem 210 is individually addressable in a compact format. In some embodiments, the emitters are separated from each by at least the diameter of optical fibers. In relation to addressability, each emitter is transitionable between an activated state for emitting light (with different output settings) and a deactivated state. However, in alternative variations of light source subsystem 210, multiple emitters can be associated with a single die physically coupled to an electronics substrate 223 to enable addressability of emitters in groups, or all emitters of the light source subsystem 210 can be associated with a single die physically coupled to the electronics substrate 223. In alternative embodiments where each emitter does not have its own die, the emitters can, however, still be individually addressable using other wiring architecture.

The emitters 212 of the light source subsystem 210 are arranged in a 2D array. The 2D array can be a square array, where the square array can have equal numbers of emitters along its width and height. The size of the array of emitters, in terms of number of emitters, distribution of emitters in space, and spacing between emitters, can be configured based on size of each individual emitter (in relation to size constraints of the wearable system), as well as morphological factors of the set of optical fibers 221 optically coupling emitters to other system components, as described in further detail below. In alternative embodiments, however, the emitters 212 can be arranged in a polygonal array, ellipsoidal array, or in any other suitable manner (e.g., an amorphous array). In an example, the emitters 212 are arranged in an 8×8 square array, spaced with a pitch of 1 mm, and collectively have a footprint of 1 cm$^2$.

The emitters 212 can operate in a continuous emission mode for continuous transmission of light. The emitters 212 can also operate in a pulsed mode, where periods of light emission are interspersed with periods of non-emission at a desired frequency. Pulses can thus be associated with one or more of: a pulse profile having width characteristics and other pulse shape aspects (e.g., peaks, troughs, etc.); power draw (e.g., in relation to power amplitude); temporal features (e.g., periodicity, frequency of pulses, etc.); and any other suitable pulse features. In a specific example, the emitters 212 operate in a pulsed mode with pulse width modulation (PWM) having a power draw of 27% efficiency at 100 mW of power output.

Figure 3:
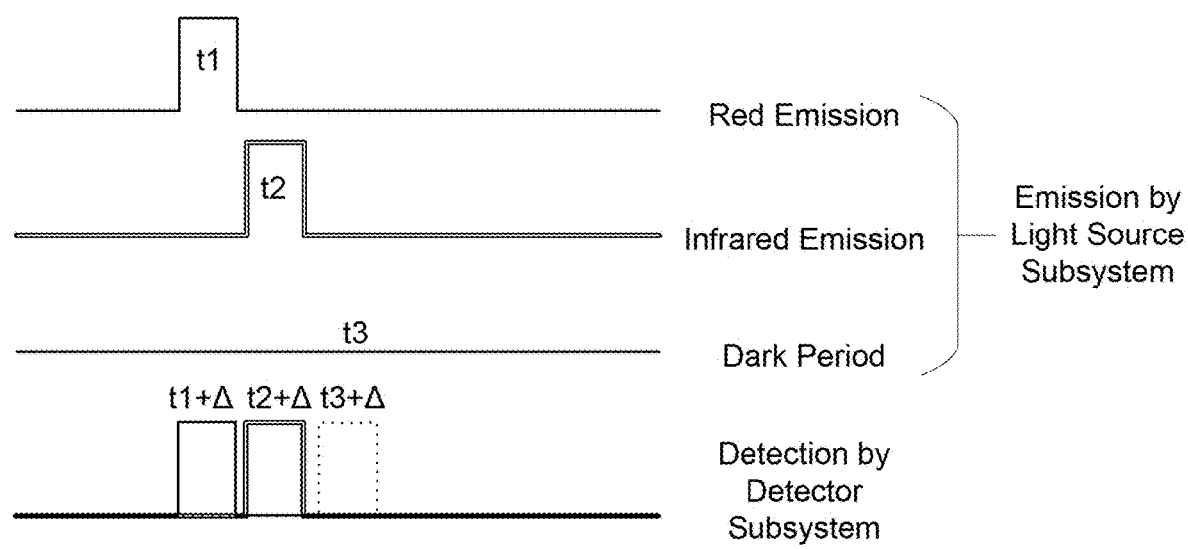
FIG. 3 depicts an example of light emission operation in relation to signal detection, in accordance with one or more embodiments.

In relation to non-continuous transmission modes, light emission by the emitters 212 of the light source subsystem 210 can be coordinated with detection by the detector subsystem, where emission of light (e.g., by a subset of emitters) is timed with light detection in phases. In one example, as shown in FIG. 3, the emitters of the light source subsystem emit a first light profile (e.g., a pulse of red light provided within a first time window), followed by a second light profile (e.g., a pulse of infrared light provided within a second time window), followed by a third light profile (e.g., dark period provided within a third time window), where each pulse and dark period is detected sequentially by an embodiment of the detector subsystem described below. As such, scanning by the detector subsystem to generate and decode light signal data can be carefully timed with operation of the light source subsystem 212.

The emitters 212 of the light source subsystem 210 can further be configured to transmit light through optical elements that manipulate light along a path of transmission to a surface of the region of interest. Optical elements can include one or more of: filters, lenses, mirrors, collimation elements, waveguides, other beam shaping elements, and any other suitable optics. As shown in FIG. 2, the emitters 212 are coupled with first ends of a set of optical fibers 221 for transmission of light to a region of interest, through the wearable interface 230 described below. Each fiber of the set of optical fibers 221 includes a glass optically transparent core. Each fiber can also include sheathing layers including one or more of: a reflective layer (e.g., to provide total internal reflection of light from a portion of the region of interest to the corresponding grouped pixel unit), a buffer layer (e.g., to protect the fiber), and any other suitable layer. Additionally or alternatively, each fiber can be separated from adjacent fibers by a material (e.g., optically opaque medium, epoxy) that prevents cross-transmission of light between fibers, and also promotes coupling between first ends of the fibers and the emitters 212 of the light source subsystem 210. As such, each fiber can be isolated (e.g., optically, thermally, etc.) from other fibers.

In morphology, each fiber 221 has a length that minimizes distance-related signal loss factors between the emitter and the region of interest. Each fiber can have a rectangular/square cross section to enable compact bundling of fibers. In a specific example, each fiber has a cross sectional width of 400 μm, thereby providing complete coverage of the apertures of the emitters, where, in a specific example, the VSCEL emitters each have 3 apertures collectively having a footprint of 50 μm in diameter; however, in alternative embodiments, the fibers can have a circular cross section or any other suitable cross section, with any other suitable dimensions.

As described below in relation to the wearable interface 230, second ends of the set of optical fibers 221 are coupled to the wearable interface in a manner that provides controlled light transmission to the region of interest associated with the wearable interface.

4.2 System—Wearable Interface

Figure 4:
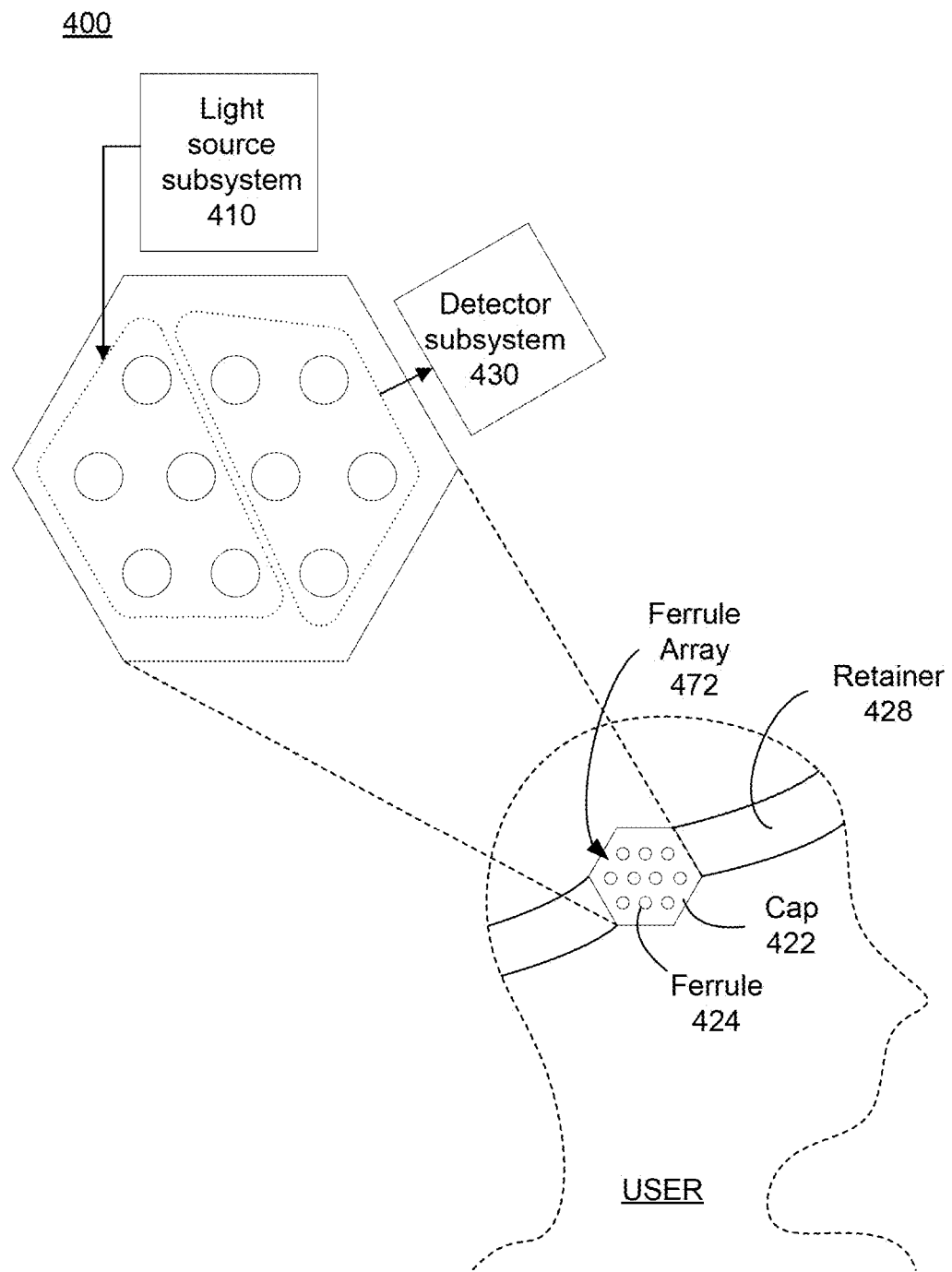
FIG. 4 depicts a schematic of an interface to a head region of a user, in accordance with one or more embodiments.

FIG. 4 depicts a head-mountable interface in accordance with one or more embodiments, where the interface 420 functions to interface light emitters of a light source subsystem 410 (such as an embodiment of the light source subsystem described above) to the head region of the user during use, and to interface the head region with a detector subsystem 430 (described in more detail below), in order to assess brain activity in a portable manner.

The interface 420 is configured to be worn by a user and includes a cap 422 and an array of ferrules 472 supported by the cap 422. The cap 422 can also include a retainer 428 configured to secure the cap 422 to the head of the user (or another body region of the user, in relation to signal detection from other body regions). As described below, a ferrule 424 of the array of ferrules 472 can include channels or other positioning features for retaining optical fibers associated with the light source subsystem 410 and/or the detector subsystem 430 in position. As such, the array of ferrules can include ferrules supporting optical fibers for transmission of light toward and/or away from the target region. The cap 422 and array of ferrules 472 also function to bias the optical fiber ends against the target regions in a manner that is comfortable to the user during use. The biasing force can be created by elastic forces provided by deformation of the cap or elastic elements coupled to or otherwise in communication with the ferrules, as described in more detail below.

FIG. 5A shows a first embodiment of the interface shown in FIG. 4. A cap 522a can be configured to couple to a user by a retainer 528a. The cap 522a includes a first broad surface 551a, a second broad surface 552a opposing the first broad surface, and an array of ports retaining an array of ferrules, including ferrule 524a. A cross sectional view (right) shows a ferrule 524a passing through the first broad surface 551a and the second broad surface 552a of the cap 522a. The ferrule 524a is retained in a port 553a of the array of ports. The ferrule 524a includes a channel 554a configured to retain a fiber optic cable 555a in position. The fiber optic cable 555a is positioned such that minimal bending or movement of the fiber optic cable 555a can occur within the channel 554a. The fiber optic cable 555a is configured to interact with the head region of a user and can be coupled to a light source subsystem and/or a detector subsystem as described in greater detail below.

The channel 554a passes through the body 514a of the ferrule 524a and terminates at an opening at an end of the ferrule 524a configured to interface with the head region of the user. In other embodiments, the channel 554a can terminate within the body of the ferrule 524a, such that the channel 554a does not have an opening at an end of the ferrule 524a configured to interface with the head region of the user. In one embodiment, a cover 556a can be coupled to an end region of the ferrule 524a, the cover configured to seal the channel 554a from the external environment in order to protect internal components (e.g., the fiber optic cable 555a). The cover 556a can also be composed of a material that provides light manipulation functions. For instance, the cover 556a can be composed of an optically transparent material that allows light transmission without significant loss. In another embodiment, the cover 556a can be composed an optically translucent material to facilitate diffusion of stimulation light. In another embodiment, one or more regions of the cover 556a can include lenses that affect light transmission through or into the cover 556a.

Figure 5B:
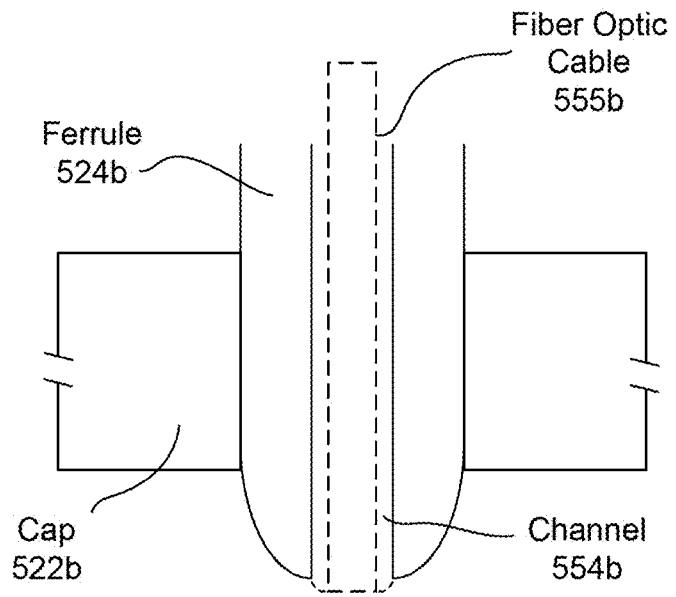
FIG. 5B depicts a schematic of a first mode of operation and a second mode of operation of an interface to a head region of a user, according to the embodiment of FIG. 5A.
Figure 5B:
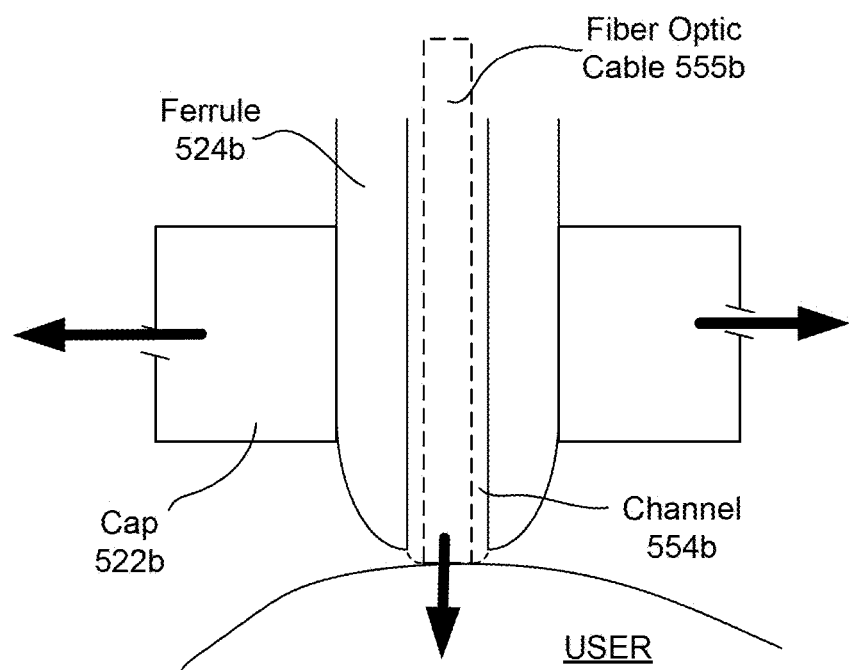

In one embodiment, such as the embodiment of FIG. 5A, the cap 522a is composed of a material that allows the cap 522a and the ferrule 524a to be biased toward a head region of a user. For example, FIG. 5B shows a relaxed state (top) and a compressed state (bottom) of an interface to a head region of a user, according to an embodiment. When a cap 522b is placed on the head region of a user, an end region of a ferrule 524b is configured to interact with the head region of a user. As shown in FIG. 5B (top), the system is in a baseline (e.g., relaxed) mode, whereby the array of ferrules is not biased toward a head region of the user. As shown in FIG. 5B (bottom), a normal force between the ferrule 524b and the head region of the user is produced by the stretching of the cap 522b (e.g., as the user stretches the cap to wear the system), such that stretching the cap produces a stressed mode of the cap assembly that biases the array of ferrules toward the head region of the user. The cap 522b material can thus be subjected to tensile and compressive forces, where tension produces a normal force that compresses the array of ferrules toward the head region of the user and supports the interaction of the ferrule 524b with the user. Then, during an operation mode of the system, a fiber optic cable 555b is retained in position in the channel 554b such that a signal can be transmitted from a first end of the fiber optic cable 555b to a second end of the fiber optic cable 555b, where either the first end or the second end of the fiber optic cable 555b is in communication with the head of the user.

Figure 5C:
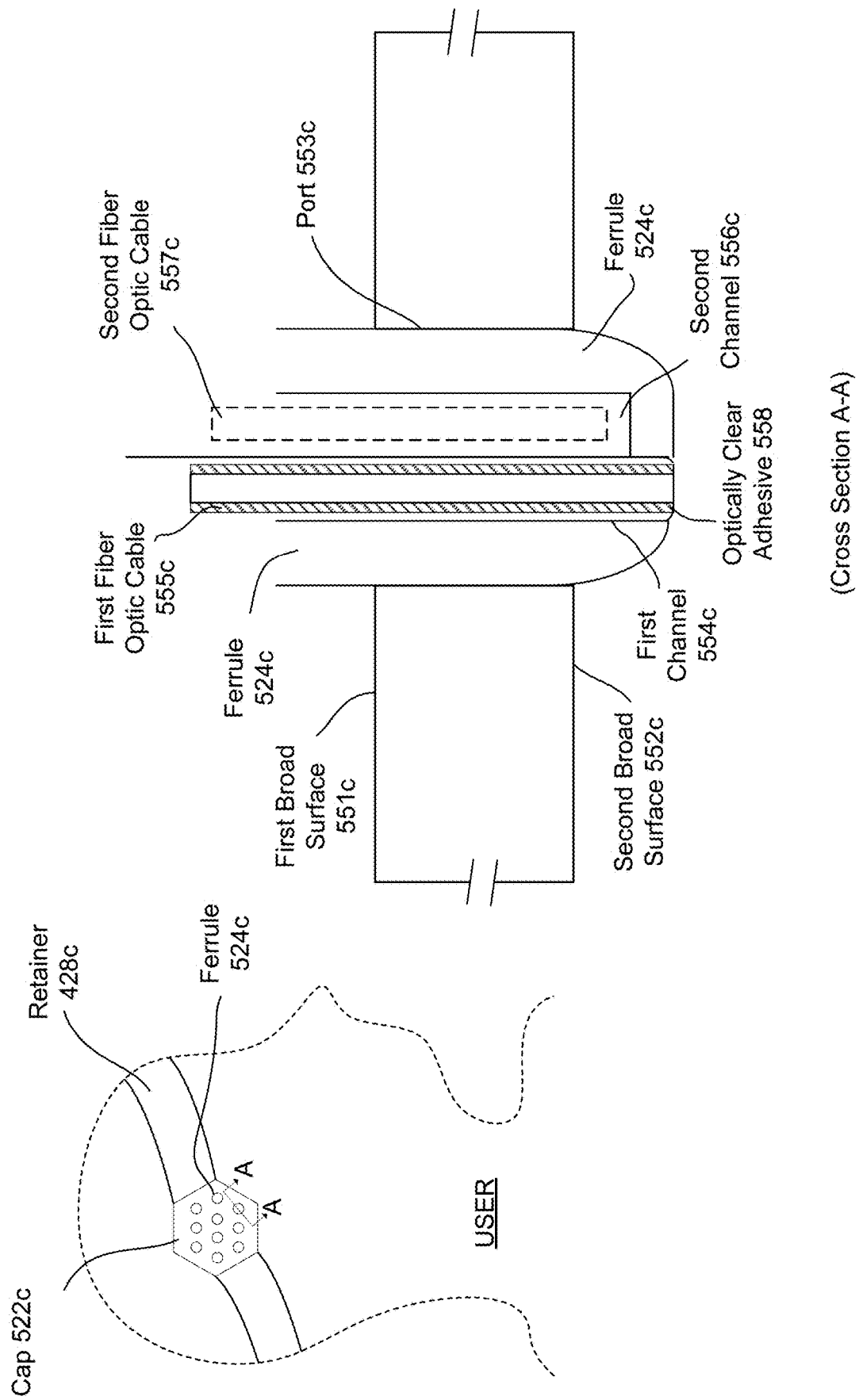
FIG. 5C depicts a schematic and cross sectional view of an embodiment of an interface to a head region of a user, according to an embodiment.

FIG. 5C shows a second embodiment of the interface shown in FIG. 4. Similar to the embodiment shown in FIG. 5A, the second embodiment includes a cap 522c that can be configured to couple to a user by a retainer 528c. The cap 522c includes a first broad surface 551c, a second broad surface 552c, and an array of ports retaining an array of ferrules. A cross section of the cap 522c (right) shows a port 553c passing through the first broad surface 551c and the second broad surface 552c. A ferrule 524c is retained in the port 553c. The ferrule 524c includes a first channel 554c and a second channel 556c where the first channel passes through the entire body of the ferrule 524c, and the second channel 556c passes through the body of the ferrule 524c and can terminate within the body of the ferrule 524c, in some embodiments.

A first fiber optic cable 555c is retained in the first channel 554c by an optically clear adhesive 558 such that the first fiber optic cable 555c can be in communication with a user during a mode of operation. For example, during a compressed state described above in relation to FIG. 5B, the first fiber optic cable 555c is optically coupled to a head region of a user for transmission of light from the head region to a detector subsystem. As such, the first fiber optic cable can be coupled to a detector subsystem, as described above in relation to FIG. 1B. The second channel 556c retains a second fiber optic cable 557c such that one end of the fiber optic cable 557c is physically isolated from the external environment and/or used to transmit stimulation light in a desired manner. The second fiber optic cable 557c can be coupled to the interior surface of the second channel 556c and/or the ferrule 524c. Additionally, the second fiber optic cable 557c can be retained in position by an optically clear adhesive. In a mode of operation, a signal can be transmitted from the user through the ferrule 524c to the second fiber optic cable. In one embodiment, the second fiber optic cable 557c can be coupled to a light source subsystem as described above in relation to FIG. 1B. The first channel 554c can be separated (e.g., optically, electrically, physically) from the second channel 556c such that signal transmission in the first fiber optic cable 555c does not interfere with signal transmission in the second fiber optic cable 557c.

Figure 6A:
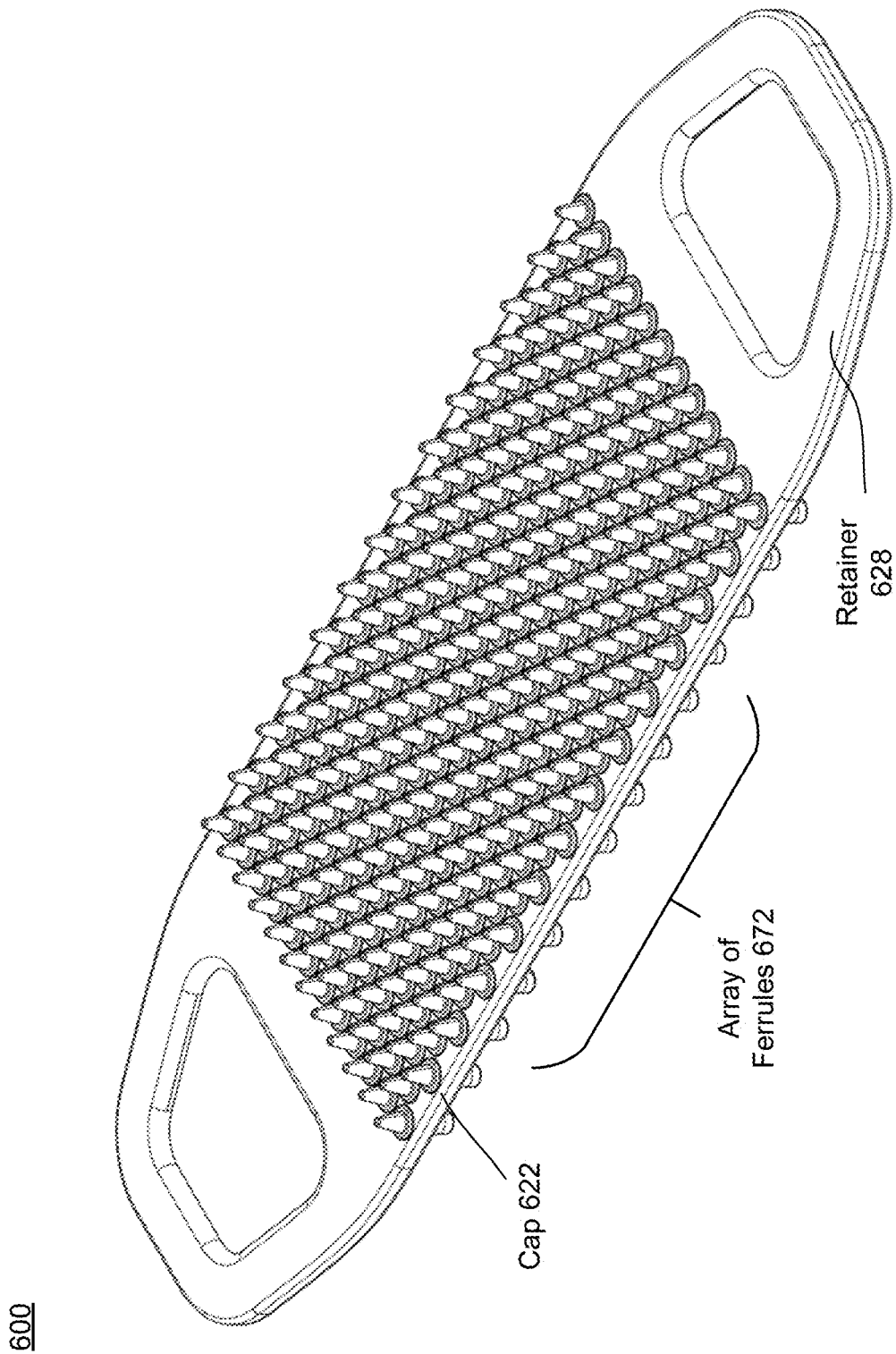
FIG. 6A depicts an isometric view of a cap, with integrated ferrules for interfacing with a head region of a user according to an embodiment.

FIG. 6A shows an isometric view from the top right of a cap and retainer assembly, according to an embodiment. The cap 622 includes an array of ferrules 672 that protrude from the first broad surface and the second broad surface of the cap 622. In one embodiment, the cap 622 and the retainer 628 are one continuous component formed as a continuum of material. In other embodiments, the cap 622 and the retainer 628 can be separate components configured to interact with each other (e.g., coupled by an adhesive, attached by a hinge mechanism, coupled to a strap, etc.).

In the embodiment shown in FIG. 6A, a portion of the array of ferrules 672 is coupled to a detector subsystem and each ferrule in the array includes a channel that extends through the body of the ferrule as described above in relation to FIG. 5A. In the embodiment, a portion of the array of ferrules 672 is coupled to a light source subsystem and each ferrule in the array of ferrules 672 includes a channel that extends partially through the body of the ferrule as described below in relation to FIGS. 6D-6E. Alternatively, a portion of the array of ferrules 672 can include a ferrule with two channels as described above in relation to FIG. 5C.

FIG. 6B shows a top view (first), a front view (second), a cross sectional view (third), and a side view (fourth) of the embodiment of FIG. 6A. The top view (first) illustrates a first broad surface 651 of a cap 622 retaining an array of ferrules 672. The array of ferrules 672 is positioned in a hexagonal configuration (e.g., close packed configuration, in the orientation shown in FIG. 6B, top). Alternatively, the array of ferrules 672 could be configured as any other type of array (e.g., rectangular array, circular array). The cap 622 is coupled to a retainer 628 by two slots 680 that can be configured to interact with a body portion of a user, such as an ear, to couple the array of ferrules 672 to the head region of the user. In alternative embodiments, the cap 622 can include a different attachment mechanism (e.g., a clip, a buckle).

The front view of FIG. 6B (top middle) illustrates the array of ferrules 672 passing through a first broad surface 651 and a second broad surface 652. The mid portion of the cross section of the array of ferrules 672 is sealed from the external environment by the cap 622. The array of ferrules 672 protrudes from the first broad surface 651 and the second broad surface 652. In other embodiments, a portion of the array of ferrules 672 can be recessed within or flush with the cap 622 for user comfort or operational purpose.

A cross sectional view (bottom middle) of FIG. 6B illustrates an internal section of a region of the cap 622. The array of ferrules 672 has a hexagonal configuration such that the ferrules appear to alternate with the cap 622 in a cross sectional view. The side view (bottom) of the assembly illustrates the cap 622 including the first broad surface 651 and the second broad surface 652.

Figure 6C:
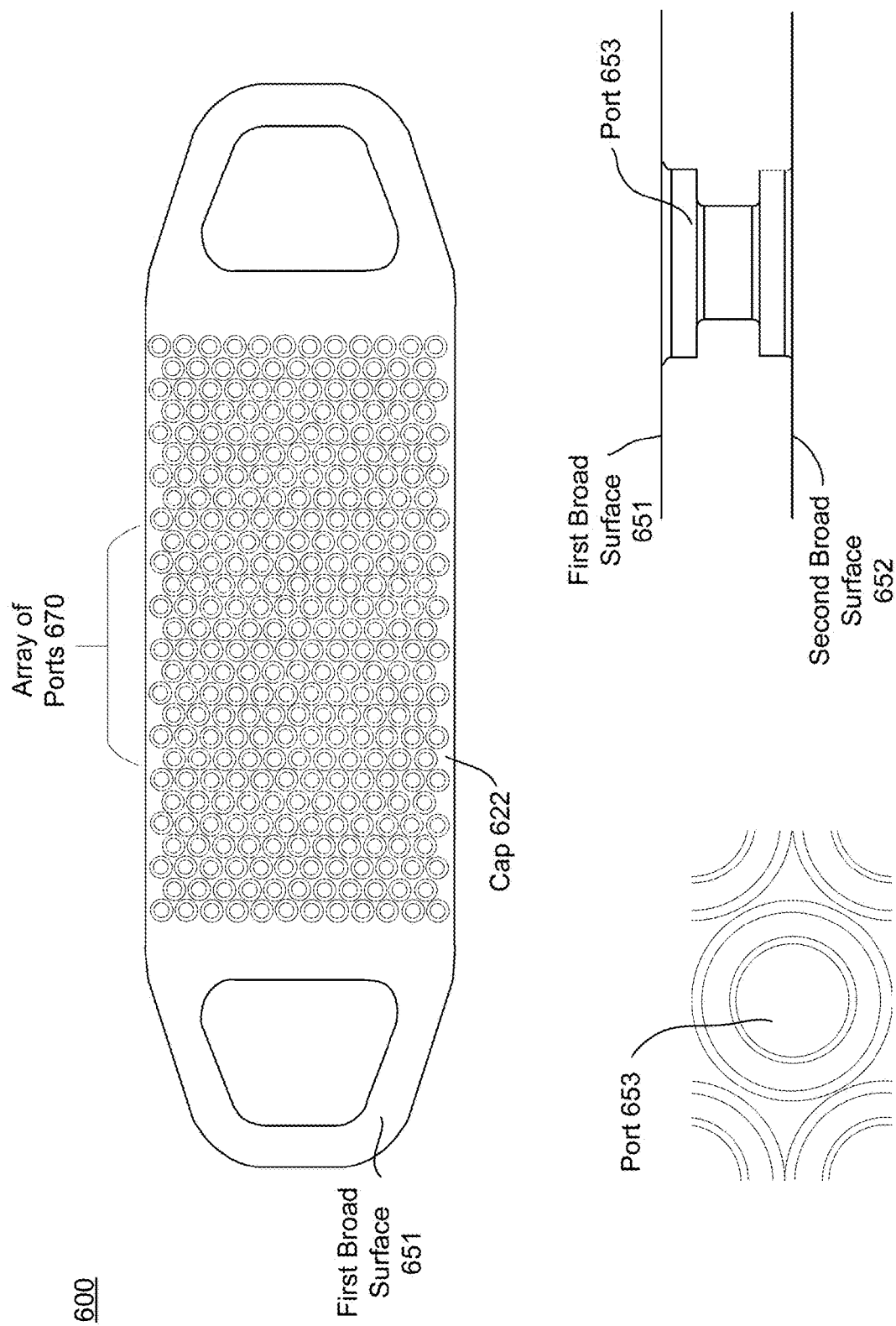
FIG. 6C depicts a top view of a cap with an array of ports, and a top view and side view of a port, according to the embodiment of FIG. 6A.

FIG. 6C shows a schematic of a cap and retainer assembly, according to the embodiment of FIG. 6A. The top view (FIG. 6C, top) illustrates a cap 622 with an array of ports 670. The array of ports 670 passes through the first broad surface 651. The array of ports 670 has a hexagonal close packed configuration in order to retain an array of ferrules. A port 653 can be shaped such that it is able to retain a ferrule of a specified size and shape. A zoomed in view (FIG. 6C, bottom left) of a port 653 illustrates the circular shape of the port 653 and the orientation of a port 653 within the array of ports 670. In alternative embodiments, a port 653 can be any shape suitable for retaining a ferrule in position. In alternative embodiments, the port 653 can be oriented such that it has more or fewer regions of adjacency with other ports (e.g., in non-hexagonal close packed configurations). A side view (FIG. 6C, bottom right) of a port 653 shows the port 653 passing through the first broad surface 651 and the second broad surface 652 of the cap 622. The width of the port 653 is largest at the first broad surface 651 and the second broad surface 652. The width of the mid-section of the port 653 is the smallest width such that a ferrule can interlock with the port 653 (e.g., in a lock-and-key mechanism), where embodiments of ferrules that interface with the cap 622 are described in more detail below. In alternative embodiments, the cap 622 can be configured to couple with a ferrule in another manner, for instance, with one or more of: an adhesive, a magnetic interface, a thermal bond, a friction-inducing interface (e.g., a press fit), and/or another manner.

In morphology, the cap 622 can be designed to fully cover the head of a user. In other embodiments, the cap 622 is designed to cover a portion of the head, depending on which location of the brain the emitters and sensors are intending to gather neural signals from, as described above. For example, if the sensors are to gather neural signals corresponding to neurons in the occipital lobe, then the head cap can be designed to reside in contact with the back of the user's head. The cap 622 and retainer 628 can also be shaped such that they can interact with other regions of the body (e.g., neck, arm, leg, etc.).

In relation to material composition, the cap 622 can be composed of a single material or a composite material to provide suitable physical properties for support of the system 600. The material can have mechanical properties (e.g., ductility, strength) suited to support interaction of the system 600 with a user. A cap 622 is configured to be worn by a user on his/her head region. As such, the cap 622 can be composed of a breathable material in order to provide comfort to the user. For example, the cap 622 can be composed of a breathable and comfortable material such as nylon or polyester.

In relation to mechanical properties, the material(s) of the cap 622 can have a compressive strength, a shear strength, a tensile strength, a strength in bending, an elastic modulus, a hardness, a derivative of the above mechanical properties and/or other properties that enable the cap 622 to deform in one or more directions without fracture and/or damage to other system 600 components (e.g., ferrule 624, fiber optic cable 655). The cap can be composed of an elastic material such as silicone, rubber, nylon, spandex, etc. In particular, the cap 622 can have an elastic modulus of 0.5-10 MPa. In alternative embodiments, the cap 622 can have an elastic modulus of any suitable value.

In relation to electrical properties, the material(s) of the cap 622 can have a conductivity, resistivity, and a derivative of the above electrical properties and/or other properties that support signal transmission through a fiber optic cable 655 retained in a channel of a ferrule. For example, the cap 622 may be composed of an insulative material in order to reduce noise interference between components of the system 622.

In relation to optical properties, the material(s) of cap 622 can have optic properties suited to facilitating signal transmission through a fiber optic cable. For instance, the cap 622 can be composed of an optically opaque material, in order to prevent excess light signals from bleeding to other portions of the system 600 in an undesired manner.

Figure 6D:
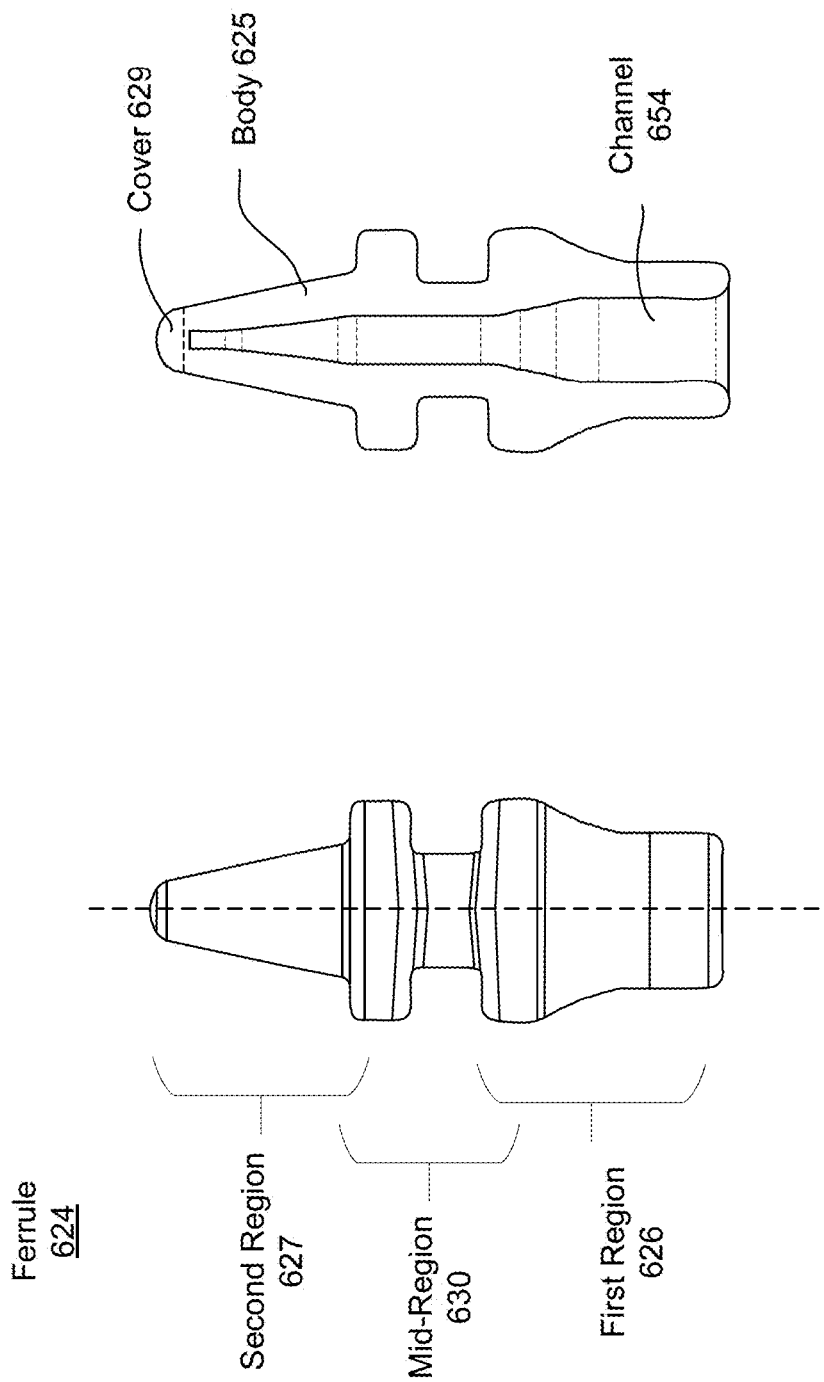
FIG. 6D depicts side and cross sectional views of a ferrule, according to the embodiment of FIG. 6A.

FIG. 6D is a schematic of a ferrule, according to the embodiment of the system shown in FIG. 6A. A side view (FIG. 6D, left) shows a ferrule 624 that can be retained in a port, such as the port 653 described above in relation to FIG. 6C. The ferrule 624 has a first region 626 and a second region 627 that are joined at a mid-region 630, where the width of the ferrule 624 is reduced at a mid-region 630 such that the ferrule 624 can interlock with a port 653. The the embodiment of FIG. 6D, the ferrule 624 has a varying width along the length of the body 625. The width of the ferrule 624 is smallest at the end of the second region 627 such that the end of the second region 627 can comfortably interact with a head region of a user. In alternative embodiments, the ferrule 624 can have a constant width along the length of the body 625 and be coupled to the cap in another manner, as described above. The ferrule 624 can also have wider or smaller end regions, depending on the design considerations of the system (e.g., manufacturability, size, material, etc.).

The ferrule 624, shown by the cross sectional view of FIG. 6D (right), includes a body 625 and a channel 654. The channel 654 terminates within the second region 627 of the body 625. Alternatively, the channel 654 can extend through the first region 626 and the second region 627 of the ferrule 624. The ferrule 624 can include a cover 629 coupled to the body 625 and/or other components within the channel 654. The cover 629 can function to seal the channel 654 from the external environment in order to protect internal components. The cover 629 can also function as the interface between the user and the ferrule 624. The cover 629 can be a separate component coupled to (e.g., by an adhesive, interlocking mechanism, etc.) or ensheathing the body 625. Alternatively, the cover 629 can be a continuous piece of the body 625.

The cover 629 can also be composed of a material that provides light manipulation functions. For instance, the cover 629 can be composed of an optically transparent material that allows light transmission without significant loss. In another embodiment, the cover 629 can be composed an optically translucent material to facilitate diffusion of stimulation light. In another embodiment, one or more regions of the cover 629 can include lenses that affect light transmission through or into the cover.

Figure 6E:
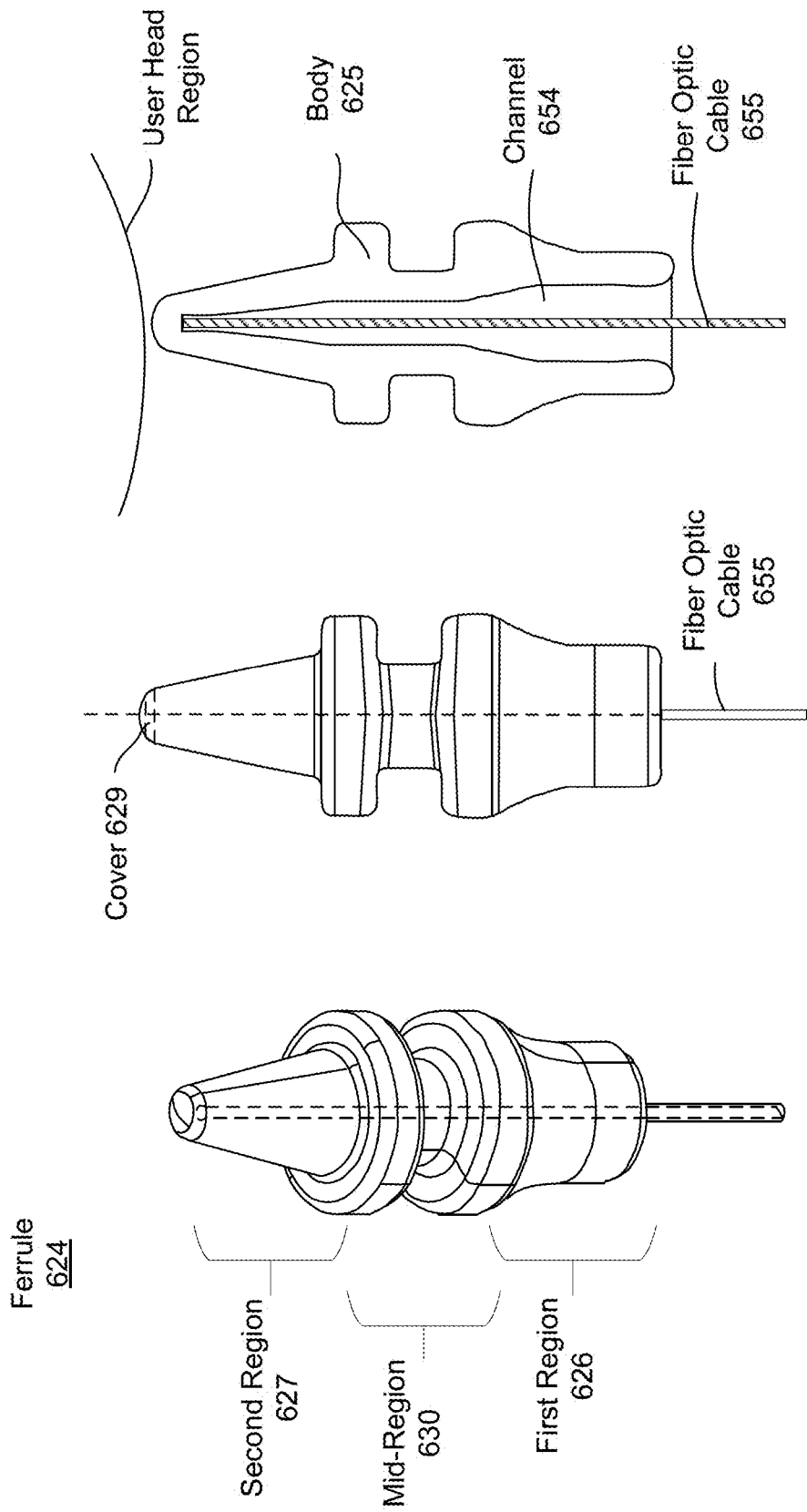
FIG. 6E depicts isometric, side, and cross sectional views of a ferrule with an integrated fiber optic cable, according to the embodiment of FIG. 6A.

FIG. 6E illustrates a ferrule including a fiber optic cable, according to the embodiment of FIG. 6A. An isometric view (FIG. 6E, left) and a side view (FIG. 6E, middle) show a fiber optic cable 655 entering through the first region 626 of the ferrule 624. The fiber optic cable 655 extends partially through the body 625 into the second region 627 of the ferrule 624. A cover 629 can be optically coupled to the fiber optic cable 655. Alternatively, the fiber optic cable 655 can be optically coupled to the body 625 of the ferrule 624. A cross sectional view (right) of the ferrule illustrates the fiber optic cable 655 retained the channel 654 of the body 625. The body 625 is configured to interact with the user head region at the second region 627 such that the fiber optic cable 655 can transmit a signal between the first region 626 of the ferrule 624, the second region 627 of the ferrule 624, and the user head region. The fiber optic cable 655 in FIG. 6E can be coupled to a light emission subsystem where light is transmitted from an end region of the fiber optic cable 655 to the head region of the user. Alternatively, the fiber optic cable 655 can be coupled to a light detection subsystem.

In morphology, the ferrule 624 can have protruding and/or recessed regions. In the embodiment of FIGS. 6D-6E, the body 625 has a recessed ring about its external perimeter that forms a portion of an interlocking mechanism such that it can mate with a port 653 of array of ports, for instance, where the port includes a protrusion about one or more portions of its internal perimeter, the protrusion operable to lock with the recess of the body 625. The width of a middle portion of the body 625 may be smaller than one or both end regions of the body 625 such that the ferrule 624 is retained in position in a port 653 without an adhesive or other attachment mechanism. In an alternative embodiment, the body 625 of a ferrule 624 has a constant width. In still other embodiments, the body 625 may be cylindrical, polygonal, or any other suitable shape for supporting the fiber optic cable 655.

In relation to material composition, the ferrule 624 can be composed of a single material or a composite material to provide suitable physical properties for supporting the fiber optic cable 655. The material can have mechanical properties (e.g., ductility, strength) suited support the fiber optic cable 655. In relation to mechanical properties, the material(s) of the ferrule 624 can have a compressive strength, a shear strength, a tensile strength, a strength in bending, an elastic modulus, a hardness, a derivative of the above mechanical properties and/or other properties that enable the ferrule 624 to move with respect to the cap 622 while maintaining its position within a port 623. In the embodiment shown in FIG. 6E, the body 625 is composed of polycarbonate; however, the body can be composed of another material (e.g., polymeric material, non-polymeric material).

In relation to electrical properties, the material(s) of the ferrule 624 can have a conductivity, resistivity, a derivative of the above electrical properties and/or other properties that support signal transmission through the fiber optic cable 655 retained in the channel 654 of the ferrule 624. The ferrule 624 may be composed of an insulative material in order to prevent excess noise from propagating from the light emission subsystem to the user and/or to other components of the system.

In relation to optical properties, the material(s) of a ferrule can have optic properties that enable signal transmission through the fiber optic cable 624. The channel 654 of the ferrule can include an optically opaque adhesive configured to facilitate signal transmission between the first region 626 and the second region 627 of the ferrule 624. The body 625 of the ferrule can also be composed of an optically opaque adhesive. In alternative embodiments, the ferrule 624 can be composed of any suitable material.

Figure 7A:
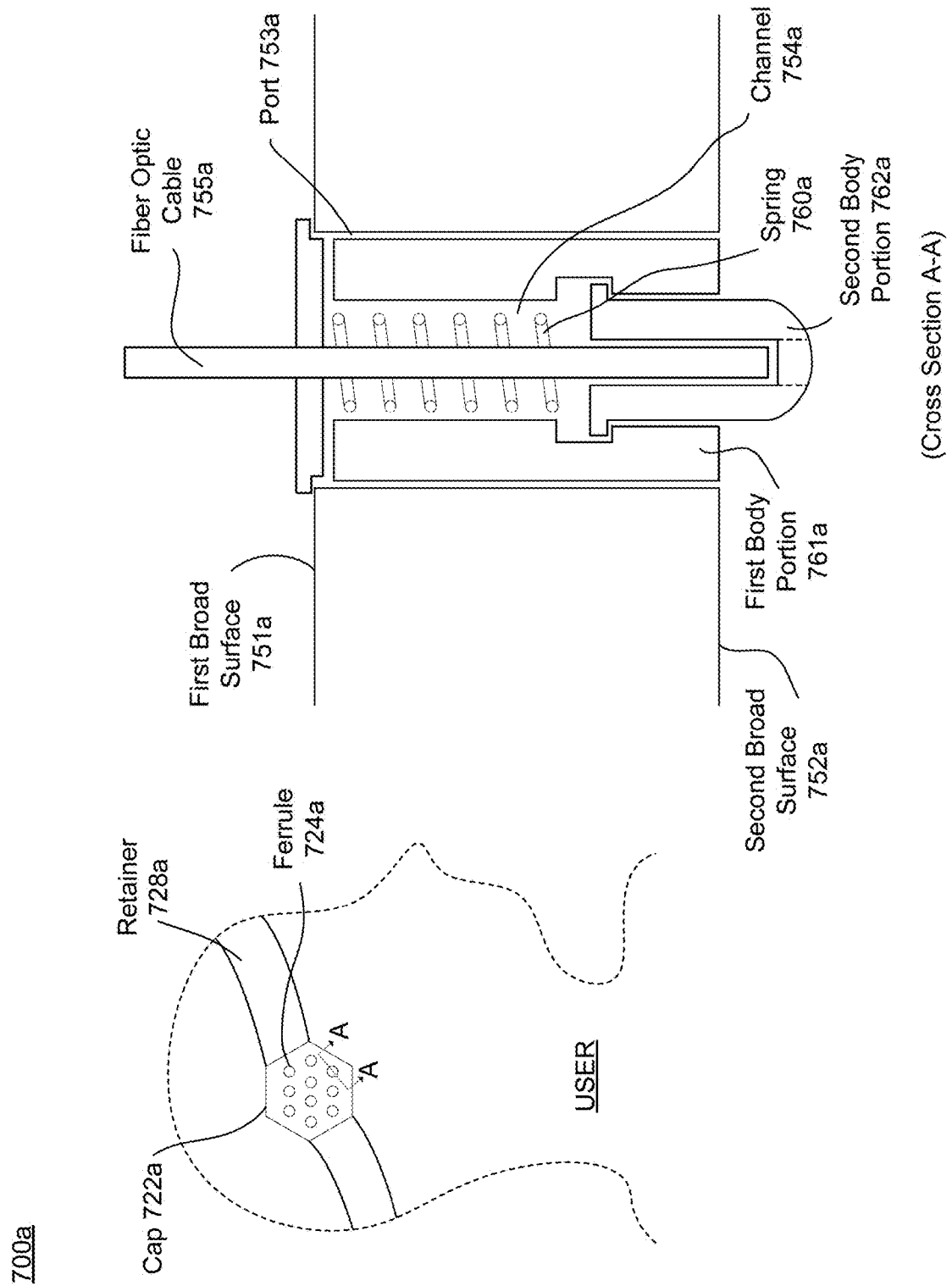
FIG. 7A depicts a schematic and cross sectional view of an embodiment of an interface to a head region of a user, according to an embodiment.

FIG. 7A shows a schematic of a cap, according to an alternative embodiment. FIG. 7A includes a cap 722a configured to a user head region by a retainer 728a. A cross section of the cap 722a shows the components of a ferrule 724a according to an embodiment. A port 753a passes through a first broad surface 751a and a second broad surface 752a of the cap 722a. The port 753a retains the ferrule 724a in position. In the embodiment of FIG. 7A, the port 753a and the ferrule 724a have the same width. In other embodiments, such as FIG. 7B described below, the width of the ferrule 724a can be smaller than the width of the port 753a at a region along the body of the ferrule 724a (e.g., in order to form a portion of a locking mechanism, as described above in relation to FIGS. 6D-6E). The port 753a and the ferrule 724a can, however, be configured in another suitable manner, in relation to mating and/or coupling with each other.

The ferrule 724a includes multiple components retained within the port 753a. The ferrule 724a has a second body portion 762a protruding from the second broad surface 752a. The second body portion 762a is coupled to a first body portion 761a of the ferrule 724a, within a channel 754a that extends through the first body portion 761a of the ferrule 724a. The channel 754a can be continuous with a cavity within the second body portion 762a, in order to allow passage of and/or retain a fiber optic cable 755a. Furthermore, as shown in FIG. 7A, the channel 754a includes a region that allows the second body portion 762a to translate relative to the first body portion 761a within a range of motion, in order to maintain coupling with the user. The channel 754a retains a spring 760a and a fiber optic cable 755a.

In one or more user modes, as described in more detail below, the spring 760a can be compressed such that the spring 760a biases a tip of the second body portion 762a against the head region of the user to allow for light transmission through the fiber optic cable 755a. Also shown in FIG. 7A, the second body portion 762a is rounded (e.g., hemispherical) such that the interaction is comfortable to the user. However, in alternative embodiments, a terminal region of the second body portion 762a can have any other suitable morphology in relation to interfacing with the body of the user.

Figure 7B:
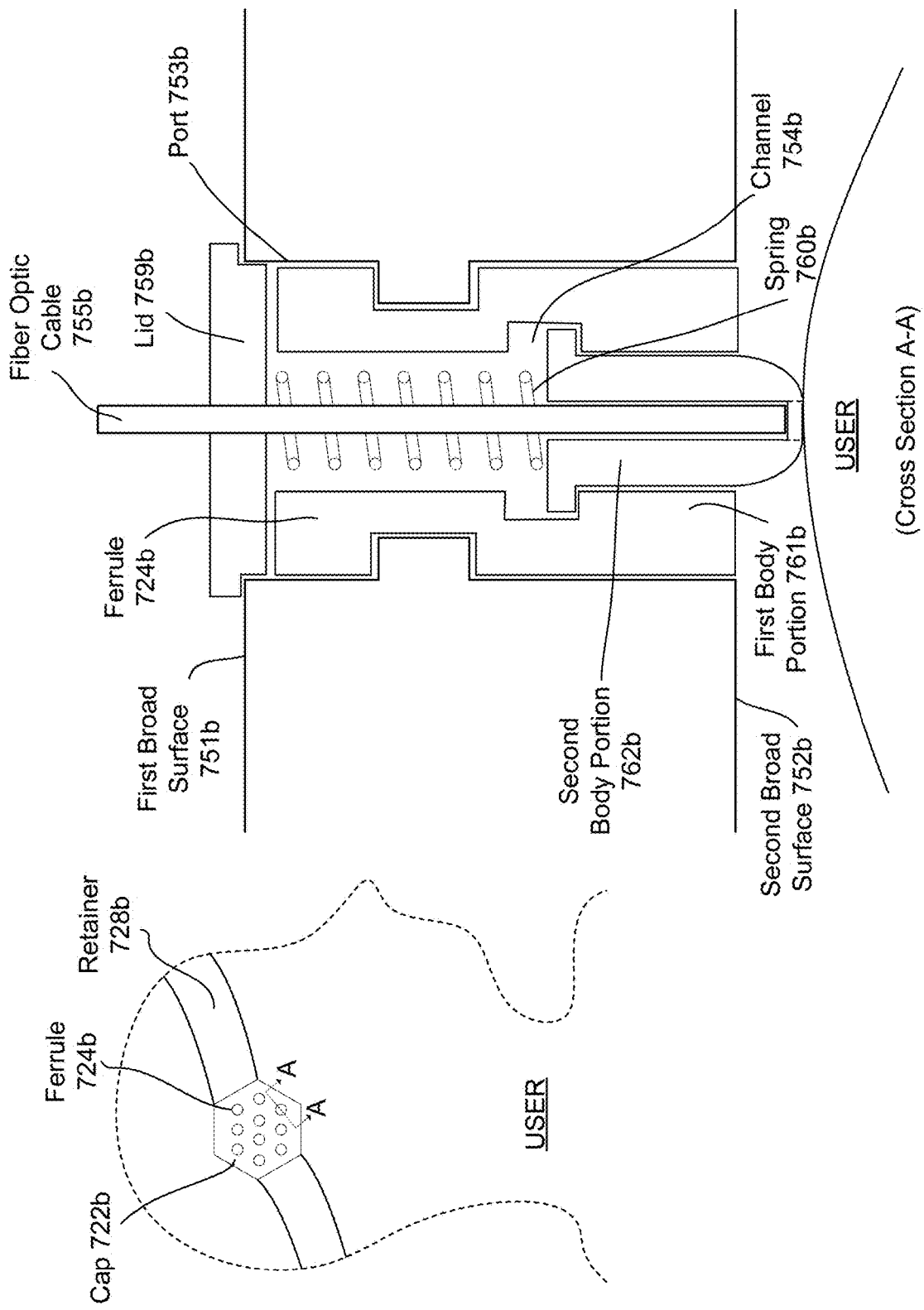
FIG. 7B depicts a schematic and cross sectional view of a variation of the embodiment of an interface to a head region of a user shown in FIG. 7A.

FIG. 7B shows a schematic of a cap, according to a variation of the embodiment shown in FIG. 7A. FIG. 7B includes a cap 722b configured to couple to a head region of a user by a retainer 728b. The cross section A-A shows a ferrule 724b retained in a port 753b in the cap 722b. The port 753b passes through the first broad surface 751b and the second broad surface 752b and is configured to retain the ferrule 724b in position. The ferrule 724b includes a channel 754b configured to retain a fiber optic cable 755b and a spring 760b. The channel 754b is sealed from the external environment by a lid 759b. The channel 754b can extend partially or completely through the first body portion 761a and the second body portion 762a of the ferrule 724b. The ferrule 724b is shaped such that it interlocks with the port 753b. A second body portion 762a of the ferrule 724b protrudes from the second broad surface 752b and is rounded to provide comfort to the user during use. During one or more use modes, the spring 760b is compressed such that the rounded end region of the ferrule 724b is coupled to a head region of a user in order to transmit signals through the fiber optic cable 755b between a user and a light emission or light detection subsystem.

Figure 7C:
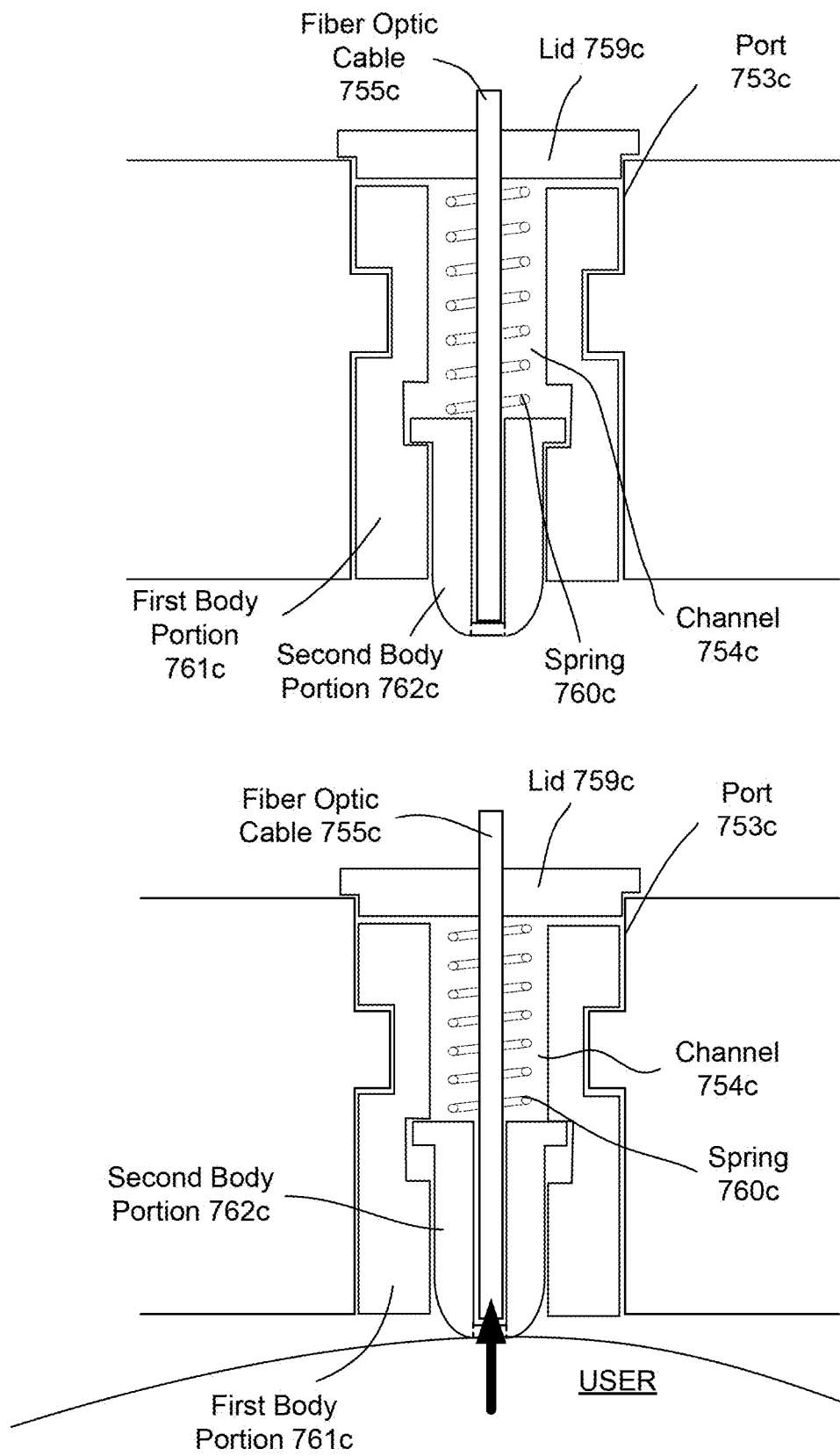
FIG. 7C depicts a first mode of operation and a second mode of operation of an interface to a head region of a user, according to the embodiment of FIG. 7B.

FIG. 7C is a schematic of a relaxed state (top) and a compressed state (bottom) of the embodiment shown in FIG. 7B. The relaxed state (bottom) shows a first body portion 761c and a second body portion 762c retained in a port 753c. A channel 754c retains a relaxed spring 760c and a fiber optic cable 755c enclosed by a lid 759c. The second body portion 762c is bias outward when a force is not exerted on the second body portion 762c. The lid 759c, the first body portion 761c, and the second body portion 762c are configured to interact such that when the system is in a relaxed state, the components are retained by the port.

In a compressed state (bottom) of FIG. 7C, the second body portion 762c interacts with a head region of a user and the spring 760c is compressed. The channel 754b allows the second body portion 762b to have a translational range of motion relative to the first body portion 761b. In the compressed state, the second body portion 762c is recessed further in the port 753c than in the relaxed state. The second body portion 762c may be flush with the first body portion 761c in a compressed state. The first body portion 761c is retained in position by the lid 759c. As such, the spring 760c and the second body portion 762c can be compressed toward the lid 759b and the first body portion 761c while the lid 759b and the first body portion 761c remain in position. A normal force is exerted between the second body portion 762c and the head of the user and the normal force compresses the spring 760c. The spring can have a spring constant ranging from 200 to 5000 N/m depending on other design components of the system (e.g., size of the channel, number of ferrules, material of the cap).

The embodiments described in FIGS. 4-7C are not exclusive or exhaustive of an interface for a head region of a user. Alternative embodiments and combinations of embodiments can exist for a device configured to transmit optic signals between a user and a subsystem. For example, the array of ferrules may be a rectangular configuration and ferrules can have a cylindrical body that does not protrude from a surface of a cap. The system may also lack some components described above in relation to FIGS. 4-7C. For instance, the system may not have a retainer. FIGS. 4-7C are provided for illustrative purposes and one skilled in the art would recognize other design possibilities.

4.3 System—Detector Subsystem

Figure 8A:
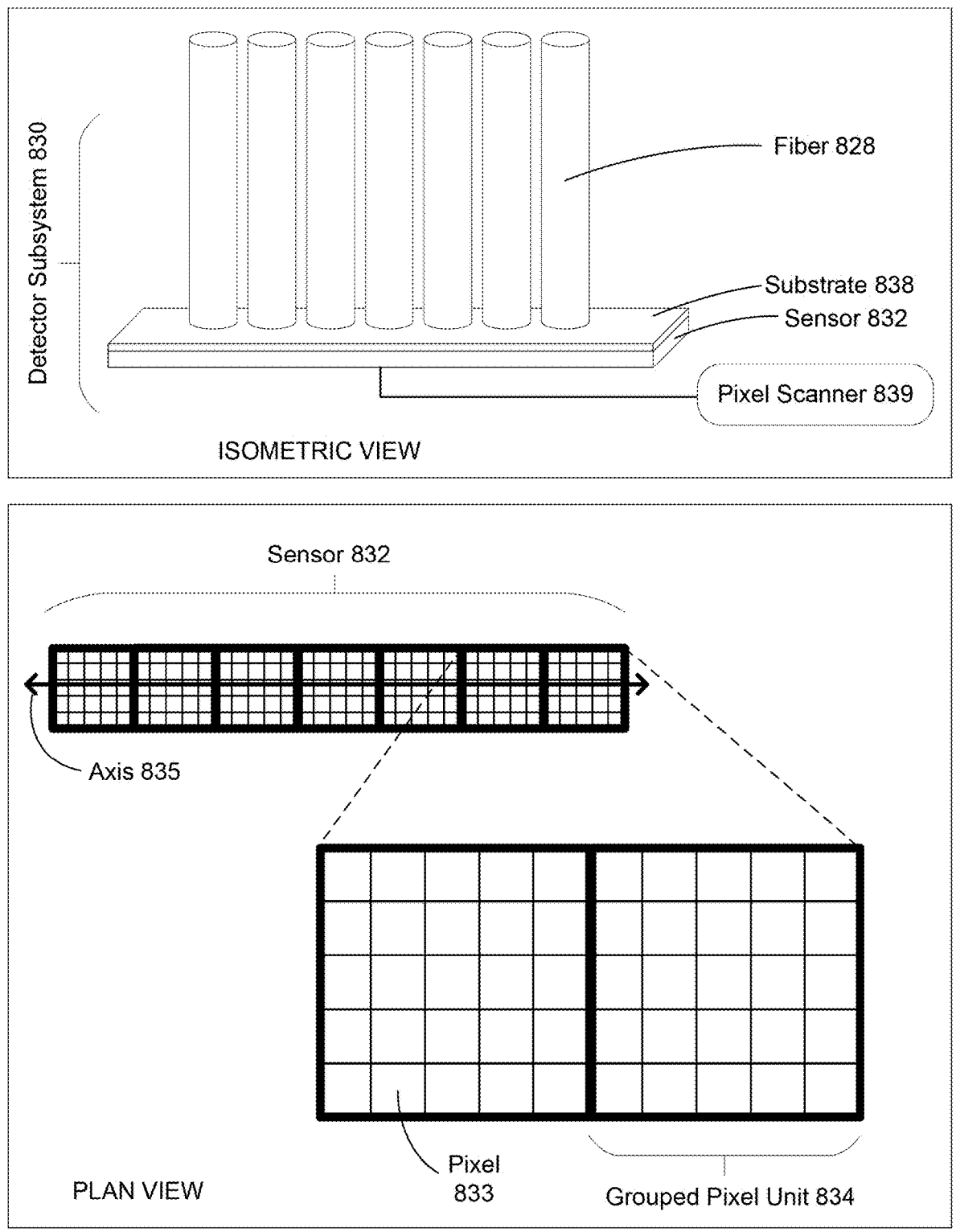
FIG. 8A depicts schematics of portions of a detector subsystem, in accordance with one or more embodiments.

FIG. 8A is a schematic of a detector subsystem 830, in accordance with one or more embodiments. The detector subsystem 830 includes one or more sensors 832. The sensor(s) 832 function to convert light to signals (e.g., electrical signals) that can be received and processed to decode brain activity of a user. The sensor(s) 832 include complementary oxide semiconductor (CMOS) architecture. However, in alternative embodiments, the sensor(s) 832 can include N-type metal-oxide-semiconductor (NMOS) architecture. In still alternative embodiments, the sensor(s) 832 can include charged coupled device (CCD) architecture, quanta image sensor (QIS) architecture, and/or any other suitable architecture for converting received light to electrical signals.

Figure 8B:
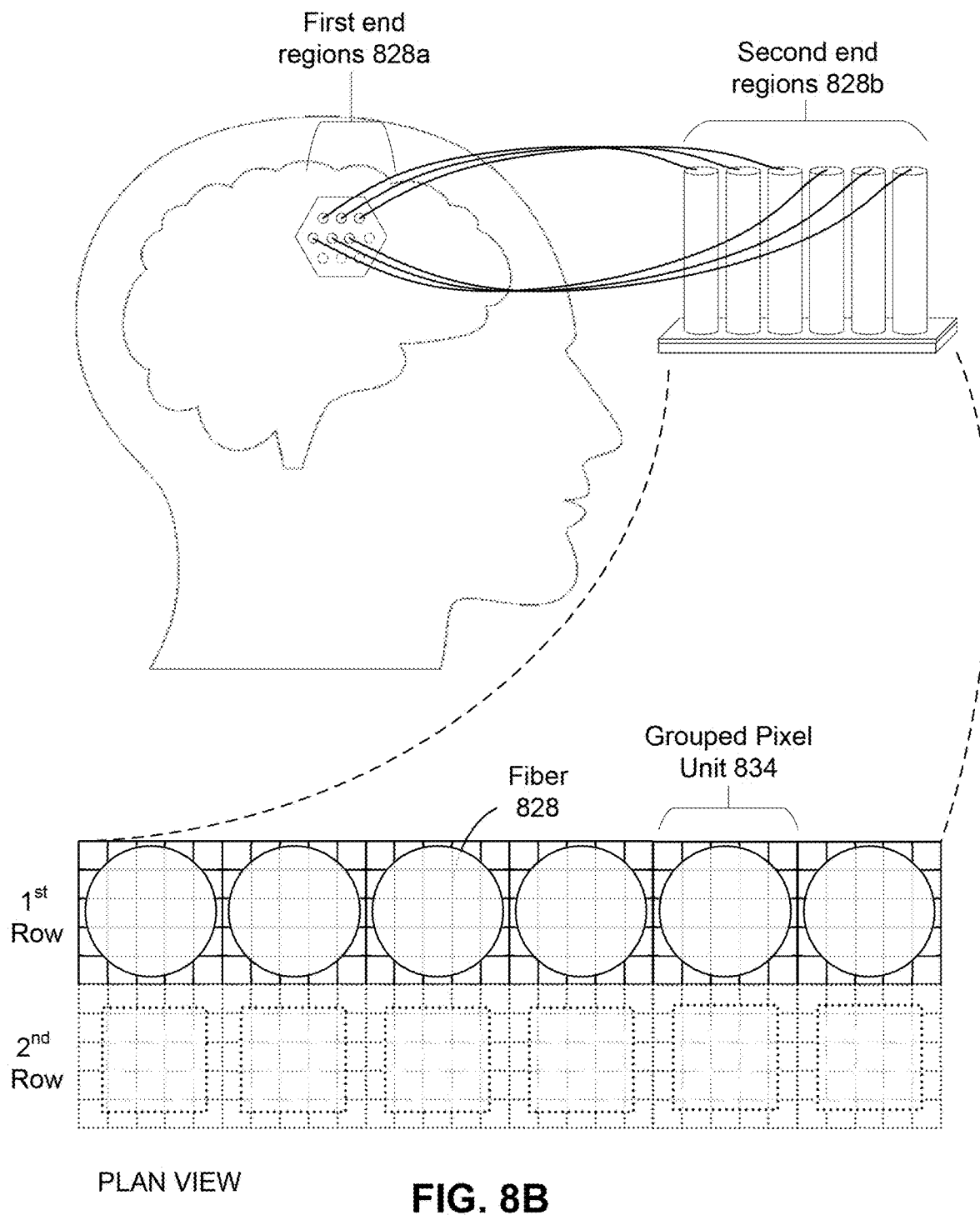
FIG. 8B depicts a schematic of portions of a detector subsystem, including multiple rows of grouped pixel units, in accordance with one or more embodiments.

In relation to CMOS architecture, the sensor(s) 832 of the detector subsystem 830 can operate in current mode or in voltage mode. To condition signals, the sensor(s) 832 can be coupled to amplifiers, attenuators, and/or any other suitable signal conditioning hardware, at the sensor level or at the pixel level. As shown in FIGS. 8A and 8B, the pixels 833 of the sensor(s) 832 are arranged into grouped pixel units, including grouped pixel unit 834. The grouped pixel units are distributed linearly along an axis 835, which improves readout efficiency to enable real-time or near real-time transmission and decoding of captured signals. However, the grouped pixel units can alternatively be distributed non-linearly (e.g., along a curve or an arc), can be distributed in a multidimensional array, or can be distributed in any other suitable manner in relation to readout from the sensor(s) 832.

The pixels 833 of a grouped pixel unit 834 are arranged in a square array, where the square array can have equal numbers of pixels along its width and height. In examples, a grouped pixel unit can have 2-100 pixels along its length and height. The size of the array of pixels corresponding to a grouped pixel unit 834 can be configured based on size of each individual pixel, as well as morphological factors of the set of optical fibers 828 corresponding to the set of grouped pixel units 834, as described in further detail below. In alternative embodiments, however, a grouped pixel unit 834 can have pixels arranged in a polygonal array, ellipsoidal array, or in any other suitable manner (e.g., an amorphous array). Each grouped pixel unit can be identically configured in relation to distribution of pixels in an array; however, in alternative embodiments, one or more grouped pixel units of the set of grouped pixel units can have an array structure that is different from others in the set of grouped pixel units.

In relation to individual pixels, the pixels preferably have a fill factor close to or equal to 100%, such that most or all of the pixel area is useable for light collection. As such, each pixel preferably has little-to-no buffer region between pixels. Each pixel also has physical characteristics that contribute to increased dynamic range, where physical characteristics include efficiency (e.g., quantum efficiency)-related parameters, capacitance-related parameters (e.g., well capacity), surface irregularity-related parameters (e.g., dark current producing irregularities), and/or any other suitable physical characteristics.

The grouped pixel units 834 are arranged in one or more linear arrays, where the linear arrays can include any suitable number of grouped pixel units. In examples, a linear array of grouped pixel units can have 2-100 grouped pixel units along its length. The size of the array of grouped pixel units can be configured based on overall sensor size limitations, in relation to providing a system in a portable and wearable form factor. In alternative embodiments, however, the array(s) of grouped pixel units 834 can be arranged in a polygonal array, ellipsoidal array, or in any other suitable manner (e.g., an amorphous array). Each array of grouped pixel units can be identically configured in relation to distribution of grouped pixel units; however, in alternative embodiments, one or more arrays of grouped pixel units can have an array structure that is different from another array of grouped pixel units.

In relation to grouped pixel units, the grouped pixel units preferably have a fill factor close to or equal to 100%, such that most or all of the grouped pixel area is useable for light collection, and no signals associated with light signal decay at a grouped pixel unit edge and/or signal cross-talk due to overlap between adjacent grouped pixel units are discarded. As such, each grouped pixel unit preferably omits a buffer region between grouped pixel units.

FIG. 8B depicts a schematic (top) of a portion of a detector subsystem and a plan view (bottom) of the portion of the detector subsystem. As shown in FIG. 8B, each grouped pixel unit corresponds to an optical fiber 828 of a set of optical fibers for light transmission. The optical fibers, as shown in FIG. 8B, include first end regions 828a mapped to a multidimensional region of interest (e.g., at a head region of a user) and second end regions 828b aligned linearly with the set of grouped pixel units. This configuration allows light from a multidimensional region of interest to be mapped to a linear array of grouped pixel units 834, in order to facilitate fast readout by the pixel scanner described below. In the embodiment shown in FIG. 8B, the fibers are mapped to the grouped pixel units in a one-to-one manner; however, in alternative embodiments, the fibers can be mapped to the grouped pixel units in any other suitable manner (e.g., not one-to-one).

Each fiber includes a glass optically transparent core. Each fiber can also include sheathing layers including one or more of: a reflective layer (e.g., to provide total internal reflection of light from a portion of the region of interest to the corresponding grouped pixel unit), a buffer layer (e.g., to protect the fiber), and any other suitable layer. Additionally or alternatively, each fiber can be separated from adjacent fibers by a material (e.g., epoxy) that prevents cross-transmission of light between fibers. As such, each fiber can be isolated (e.g., optically, thermally, etc.) from other fibers.

In morphology, each fiber 828 has a length that minimizes distance-related signal loss factors between the region of interest and corresponding sensor region. Each fiber can have a rectangular/square cross section to enable compact bundling of fibers. In a specific example, each fiber has a cross sectional width of 400 µm; however, in alternative embodiments, the fibers can have a circular cross section or any other suitable cross section, with any other suitable dimensions.

As shown in FIG. 8A, the set of fibers can be coupled to a substrate 838, where the substrate 838 is positioned between the set of fibers and the grouped pixel units of the sensor 832. The second end regions 828b of the set of fibers can be bonded (e.g., thermally bonded) to the substrate 838 or otherwise coupled to the substrate 838 in any other suitable manner. The substrate 838 is composed of an optically transparent material with high transmittance. The substrate 838 is also composed of a rigid material. The substrate 838 can also have thin cross section along light transmission paths between the set of optical fibers and the sensor 832, in order to position the second fiber end regions 828b as close to the grouped pixel units 834 of the sensor 832 as possible, to minimize divergence of light transmitted through the ends of the fibers to the sensor 832, and/or to prevent reflections from opposing surfaces (e.g., foreplane surfaces, backplane surfaces) of the substrate 832. As such, the substrate 838 functions to provide suitable optical properties for light transmission from the set of fibers, retain positions of the set of fibers relative to the grouped pixel units 834 of the sensor 832, and can additionally function to mechanically support the set of fibers and/or sensor 832 (e.g., in relation to attenuating or removing transmission of forces between the set of fibers and the pixels 833 or grouped pixel units 834 of the sensor 832).

In a specific example, the substrate 838 is an alkali-free flat glass that has a thickness of 0.03 mm along a direction of light transmission between the set of fibers and the sensor 832. The substrate 838 is polished to have low roughness, has a coefficient of thermal expansion of 2.6E-6/° C., and is usable in applications involving temperatures of up to 600° C. However, in alternative embodiments, the substrate 838 can be composed of any other suitable material, have any other suitable optical, thermal, or physical properties, have any other suitable thickness, have any other suitable rigidity, and be processed in any other suitable manner.

Material and morphological features of the fibers 828 and/or the substrate 838 cooperate to control and reduce light divergence of light incident on the sensor 832. The fibers 828 and/or the substrate 838 can additionally or alternatively support a multi-wavelength (e.g., dual wavelength) light transmission mode of the system in order to control light divergence.

As shown in FIG. 8A, the detector subsystem 830 also includes a pixel scanner 839. The pixel scanner 839 is a line scanner that reads electrical signals produced by the grouped pixel units 834 of the sensor 832 in order to generate neural stream data that can be processed by the computing system described above. The pixel scanner 839 can read each grouped pixel units of a row of grouped pixel units sequentially and/or linearly, in order to produce fast readout speeds.

As such, the pixel scanner 839 can be specified with parameters related to speed (e.g., in terms of frame rate), power consumption, or any other suitable parameter. In a specific example, the pixel scanner 839 can read a row of grouped pixel units within 10 µs at a frame rate of 2500 Hz; however, alternative embodiments of the pixel scanner 839 can read rows of grouped pixel units with any other suitable speed.

The detector subsystem 830 is thus operable in a line scanning mode. In relation to the line scanning mode, one or more grouped pixel units can be saturated by incident light that travels from the region of interest, through the set of fibers 828, and to the sensor 832. Additionally or alternatively, in relation to the line scanning mode, edge regions of a first grouped pixel unit can receive light signals associated with a second grouped pixel unit (e.g., a grouped pixel unit adjacent to the first grouped pixel unit), where crosstalk associated with overlapping signals from different grouped pixel units can be processed to isolate signal features specific to a grouped pixel unit using signal processing methods described below.

As such, as described in more detail in relation to the methods of Section 3.3.1 and 4 below, the detector subsystem 830 can, during characterization of the region of interest, have a configuration where a central region of a first grouped pixel unit of the set of grouped pixel units is saturated by light from one of the set of optical fibers. Operating in a saturated mode can significantly increase dynamic range of the detector subsystem 830. Additionally or alternatively, the detector subsystem 830 can, during characterization of the region of interest, have a configuration where an unsaturated edge region of the first grouped pixel unit receives light associated with a second grouped pixel unit adjacent to the first grouped pixel unit, and the pixel scanner 839 transmits light-derived signals from the central region and the unsaturated edge region of the first grouped pixel unit for characterization of the region of interest. Thus, the system can operate with saturated grouped pixel units and/or crosstalk across grouped pixel units while still allowing extraction and decoding of signals that are characteristic of brain activity of a user who is interacting with the system.

4.3.1 Signal Generation Methods of Detector Subsystem

As described above, FIG. 9 depicts a flow chart of a method 900 for generating and processing optical signals, in accordance with one or more embodiments. The method 900 functions to enable decoding of optical signal-derived data from a region of interest, using high dynamic range sensors and individually addressable light sources of a compact system.

Figure 9:
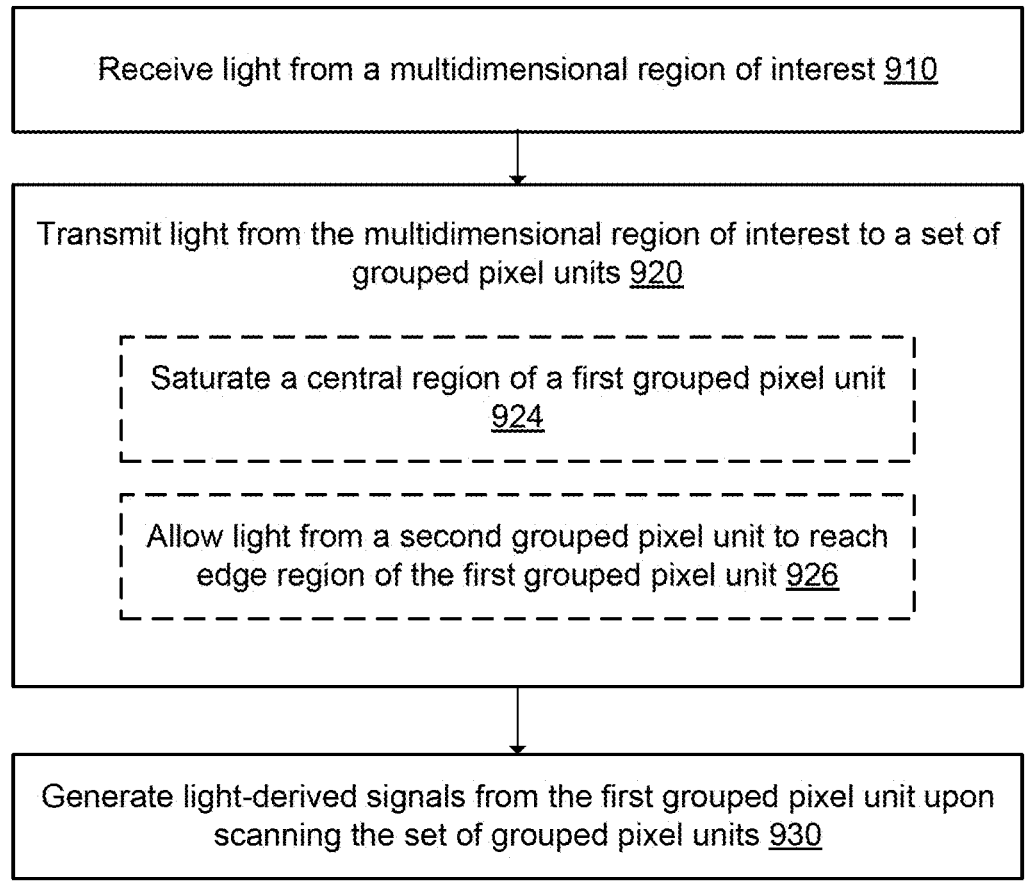
FIG. 9 depicts a flow chart of a method for generating and processing optical signals, in accordance with one or more embodiments.

As shown in FIG. 9, the detector subsystem, through first ends of a set of optical fibers, receives 910 light from a multidimensional region of interest, which functions to provide controlled transmission of light that can be received by a sensor for characterization of the region of interest. The light transmitted from the multidimensional region of interest can include light in the non-visible spectrum and/or light in the visible spectrum, can include a single wavelength of light or multiple wavelengths of light, can include naturally encoded information (e.g., due to physiologically induced phenomena), and/or can include synthetically encoded information (e.g., due to polarization or other light manipulating optics positioned along a light transmission pathway). The transmitted light can be associated with any energy associated factors (e.g., power, duration of transmission, intensity), waveform factors (e.g., pulsed, non-pulsed, waveform shape), temporal factors (e.g., frequency of signal transmission), and/or any other suitable factors.

In relation to the interface described above, the multidimensional region of interest is a head-region of the user, where noninvasively-acquired light signals can be used to decode brain activity of the user through the head region. The head region can include one or more of: a frontal region, a parietal region, a temporal region, an occipital region, an auricular region, an orbital region, a nasal region, or an infraorbital region. Additionally or alternatively, the head region can include other cranial or facial regions including one or more of: an oral region, a parotid region, a buccal region, or any other suitable region of the head of the user. In alternative embodiments, the multidimensional region of interest can be associated with another anatomical region of the user. Additionally or alternatively, the multidimensional region can be associated with a surface or volume of material of another object.

The optical fibers can transmit light derived from light that has originated at the set of light emitters and interacted with the multidimensional region of interest (e.g., the head of the user). The transmitted light can thus be associated with light sourced from individually addressable emitters, where light output from the emitters can be timed according to pixel scanning of the detector according to methods described below. The optical fibers can additionally or alternatively transmit light derived from ambient light from the environment of the user, where the ambient light has interacted with the multidimensional region of interest. Light transmission through the set of optical fibers can, however, come from any other suitable source.

As shown in FIG. 9, the optical fibers transmit received light 920 to an array of pixels of the detector subsystem. The array of pixels include CMOS pixels, but can alternatively include CCD pixels or pixels having any other suitable sensor architecture. The pixels can be arranged linearly along an axis as a set of grouped pixel units, where the arrangement of pixels as grouped pixel units is described above. However, the array of pixels can alternatively be configured in another manner.

Light is transmitted through second ends of the set of optical fibers toward the sensor for generation of electrical signals that are processed to decode information from the region of interest. The second ends can be positioned as closely as possible to the sensor to minimize adverse effects of light divergence due to distance between the fiber ends and the sensor. In relation to elements described above in relation to the sensor, the detector subsystem can transmit light through second ends of the set of optical fibers, through a thin glass substrate, and toward the grouped pixel units of the sensor, in order to reduce light divergence effects and in order to provide robust positioning and alignment of the fibers relative to the grouped pixel units of the sensor.

Figure 10A:
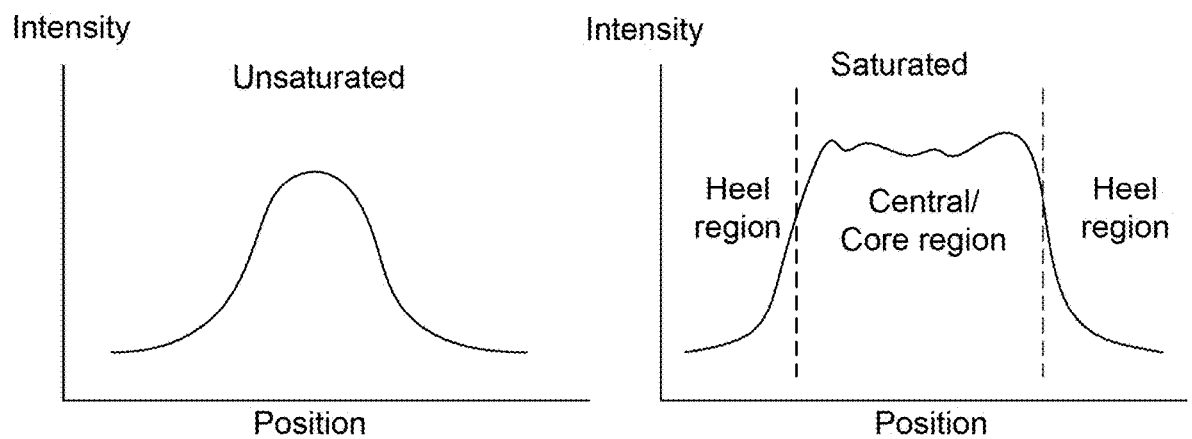
FIG. 10A depicts unsaturated and saturated profiles of grouped pixel unit outputs, in accordance with one or more embodiments.

As shown in FIG. 9, the detector subsystem can also saturate 924 a central region of one or more grouped pixel units of the set of grouped pixel units, by allowing transmission of high power/high intensity light to the one or more grouped pixel units. In the example shown in FIG. 10A, the profile (e.g., intensity profile) of light transmitted to a first grouped pixel unit can have a top hat shape in an unsaturated scenario (FIG. 10A, left) and a truncated top hat state in a saturated scenario (FIG. 10A, right). The sensor of the detector subsystem can thus still operate in a mode where one or more grouped pixel units are saturated, which provides a significant increase in dynamic range of the sensor, and where features of the heel region and/or saturated central region are extracted during signal processing to decode information from the region of interest, as described in more detail below.

Figure 10B:
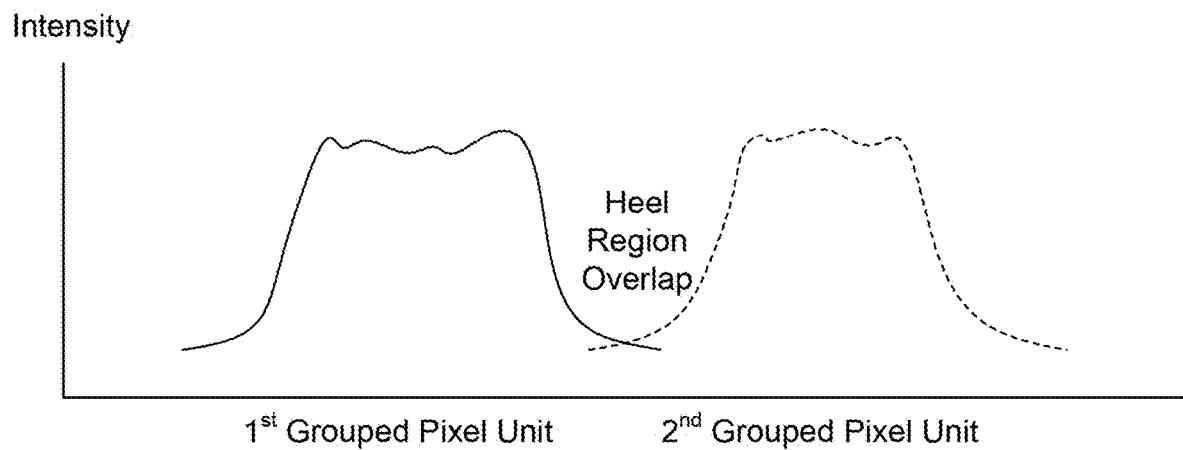
FIG. 10B depicts overlap in outputs associated with different grouped pixel unit, in accordance with one or more embodiments.

As shown in FIG. 9, the detector subsystem can also allow 926 light that is associated with a second grouped pixel unit to be received at the first grouped pixel unit, where crosstalk across the grouped pixel units can be deconstructed or isolated due to determined characteristics of the signals received at the grouped pixel units. For instance, if the heel region characteristics are known for a saturated or unsaturated intensity profile for one grouped pixel unit, relevant portions of the unsaturated intensity profile can be removed from another grouped pixel unit associated with crosstalk, in order to isolate the other grouped pixel unit's features. FIG. 10B shows an example where the heel regions (and/or other regions) of light intensity received overlap between two grouped pixel units. The first grouped pixel unit and the second grouped pixel unit associated with the overlap can be adjacent to each other or can alternatively be not adjacent to each other. Furthermore, the overlap can be associated with unsaturated edge regions of the grouped pixel units involved in the overlap, or can be associated with any other suitable region of a grouped pixel unit.

After light is transmitted 920 to the grouped pixel units, the detector subsystem can generate 930 light-derived signals for characterization of the region of interest, upon scanning the set of grouped pixel units. The scanning operation(s) of the detector subsystem provide fast readout of the array of grouped pixel units, in order to facilitate rapid processing and decoding of information (e.g., neural stream data) derived from incident light on the grouped pixel units.

In generating 930 light-derived signals, the pixel scanner reads electrical signals produced by the grouped pixel units of the sensor. The pixel scanner reads each grouped pixel units of a row of grouped pixel units sequentially in order to produce fast readout speeds. Furthermore, the pixel scanner reads the grouped pixel units in a linear manner. However, in alternative embodiments, the pixel scanner can read grouped pixel units in any other suitable order or along any other suitable path. The scanning operation can read full frames of signals for each grouped pixel unit and/or can read less than full frames of signals (e.g., a central line of signals along the scan path) for one or more of the grouped pixel units. The scanning operation can be specified with parameters related to speed (e.g., in terms of frame rate), power consumption, or any other suitable parameter. In a specific example, the pixel scanner reads a row of grouped pixel units within 10 µs at a frame rate of 2500 Hz. However, the pixel scanner can alternatively read grouped pixel units with any other suitable frame rate (e.g., greater than 100 Hz, greater than 500 Hz, greater than 1000 Hz, greater than 2000 Hz, greater than 3000 Hz, etc.).

As described above, the detector subsystem, with the pixel scanner, can be configured to coordinate scanning operation with light output through individually addressable light emitters (e.g., light emitters of the VCSEL array, LED light emitters, etc.). As such, to generate 930 the light-derived signals, a portion (e.g., a first subset) of light emitters are activated and the detector subsystem scans the grouped pixel units in coordination with activation of the portion of light emitters. Then, a second portion (e.g., a subset the same as or different from the first subset) of light emitters are activated and the detector subsystem scans the grouped pixel units in coordination with activation of the second portion of light emitters. In this example, portions of light emitters can be activated in a manner to minimize crosstalk/interference due to light emission through fibers toward adjacent grouped pixel units, or to serve any other suitable purpose. However, the first portion and the second portion of light emitters activated can be associated with targeting different portions of the region of interest (and not necessarily to minimize crosstalk/interference). However, in alternative embodiments, coordination of timing between light emission and scanning by the detector system can be conducted in any other suitable manner.

In relation to embodiments shown in FIG. 10B, generating light-derived signals can facilitate extraction of features from saturated grouped pixel units, where features can be extracted from saturated central regions and/or unsaturated edge regions of the grouped pixel units in order to increase dynamic range of the sensor outputs by several orders of magnitude relative to unsaturated sensor configurations. Features related to saturated portions can include positions of boundaries between a saturated central region of a grouped pixel unit and unsaturated edge regions of the grouped pixel unit (indicative of total power), diameter of a saturated central region of a grouped pixel unit, projected area of a saturated central region of a grouped pixel unit, or any other suitable shape-related features associated with the saturated central region. Features related to unsaturated edge regions of the grouped pixel units can include positions of boundaries between unsaturated edge regions of the grouped pixel unit, slope related features (e.g., rates of decay) of a heel portion of an unsaturated edge region, features related to integrated areas under an intensity curve corresponding to unsaturated edge regions, or any other suitable shape-related features associated with the unsaturated edge region. While features associated with intensity are described above, features that can be derived from the generated light signals can include features of any other suitable light-related parameter. Furthermore, in relation to the region of interest being at a head region of the user, the features of interest can be decoded to distinguish different types of brain activity of the user, which can be used as control inputs for controlling operation states of other systems (e.g., virtual assistants, interactions with an online social network, smart home devices, etc.). As described in more detail in relation to FIGS. 14A-14E below.

Figure 11A:
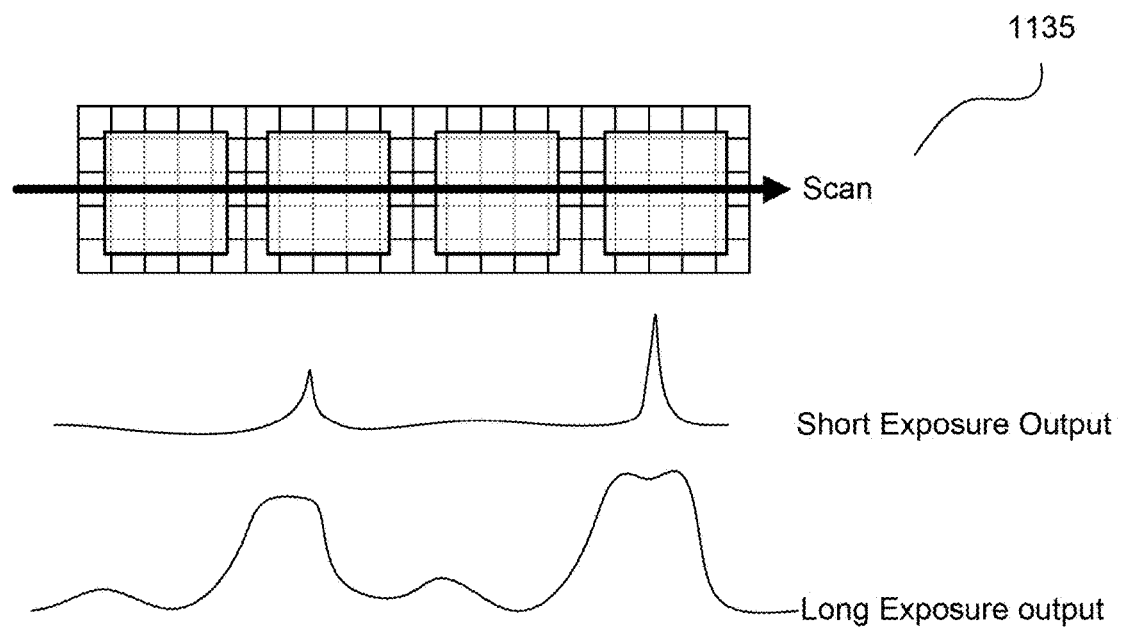
FIG. 11A depicts scanning operation with different exposure settings, in accordance with one or more embodiments.
Figure 11B:
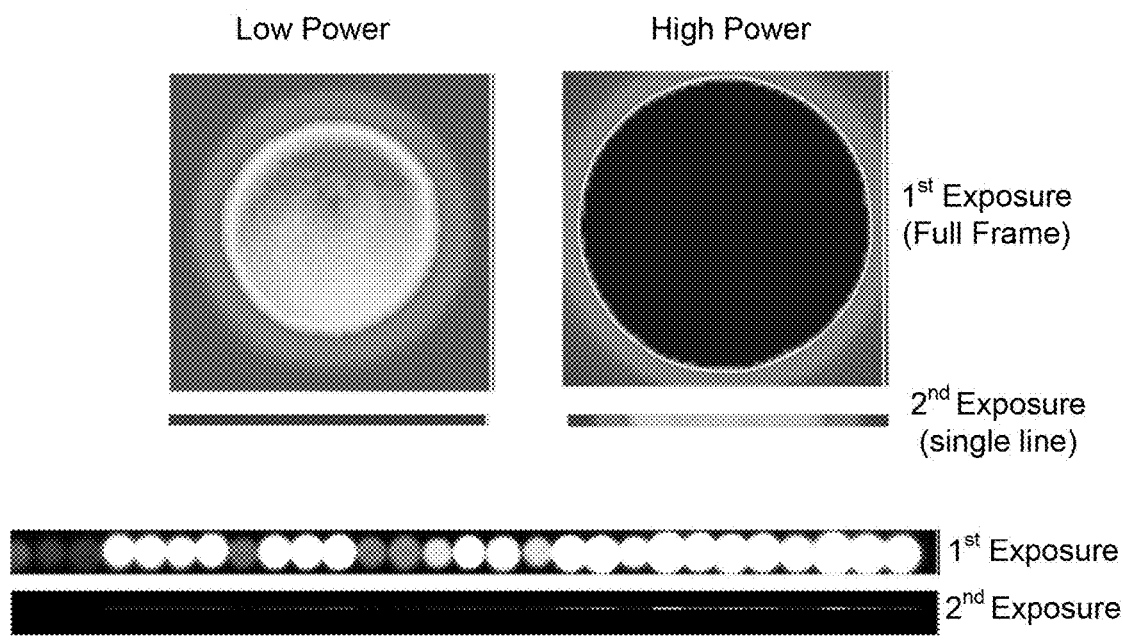
FIG. 11B depicts scanning operation with different exposure settings, different power settings, and different frame settings, in accordance with one or more embodiments.

As shown in FIGS. 11A and 11B, generating light-derived signals can also include generating 1135 light-derived signals associated with multiple light exposure levels. FIG. 11A depicts an example where the detector subsystem exposes grouped pixel units to light with a short exposure setting and the pixel scanner reads the grouped pixel units to extract features associated with the short exposure setting. As shown in FIG. 11A, the detector subsystem also exposes grouped pixel units to light with a long exposure setting, and the pixel scanner reads the grouped pixel units to extract features associated with the long exposure setting. FIG. 11B shows an example where the detector subsystem exposes grouped pixel units to light with different power settings (e.g., a low power setting, a high power setting) and scans grouped pixel units with different exposure settings, where the scans can be full frame or less than full frame. The total time associated with this operation is equal to the total time of exposures added to the total time for each scan, which is on the order of 1.82 ms per full frame scan. Features can thus be rapidly extracted and decoded from scans associated with multiple power settings, multiple exposure settings, full frame scans, and/or less-than-full frame scans, in order to characterize the region of interest.

4.4 System—Other Sensors

As shown in FIG. 1A, the system can include additional sensors 140a for detecting user behaviors and/or other biometric signals that can supplemental data.

Figure 12A:
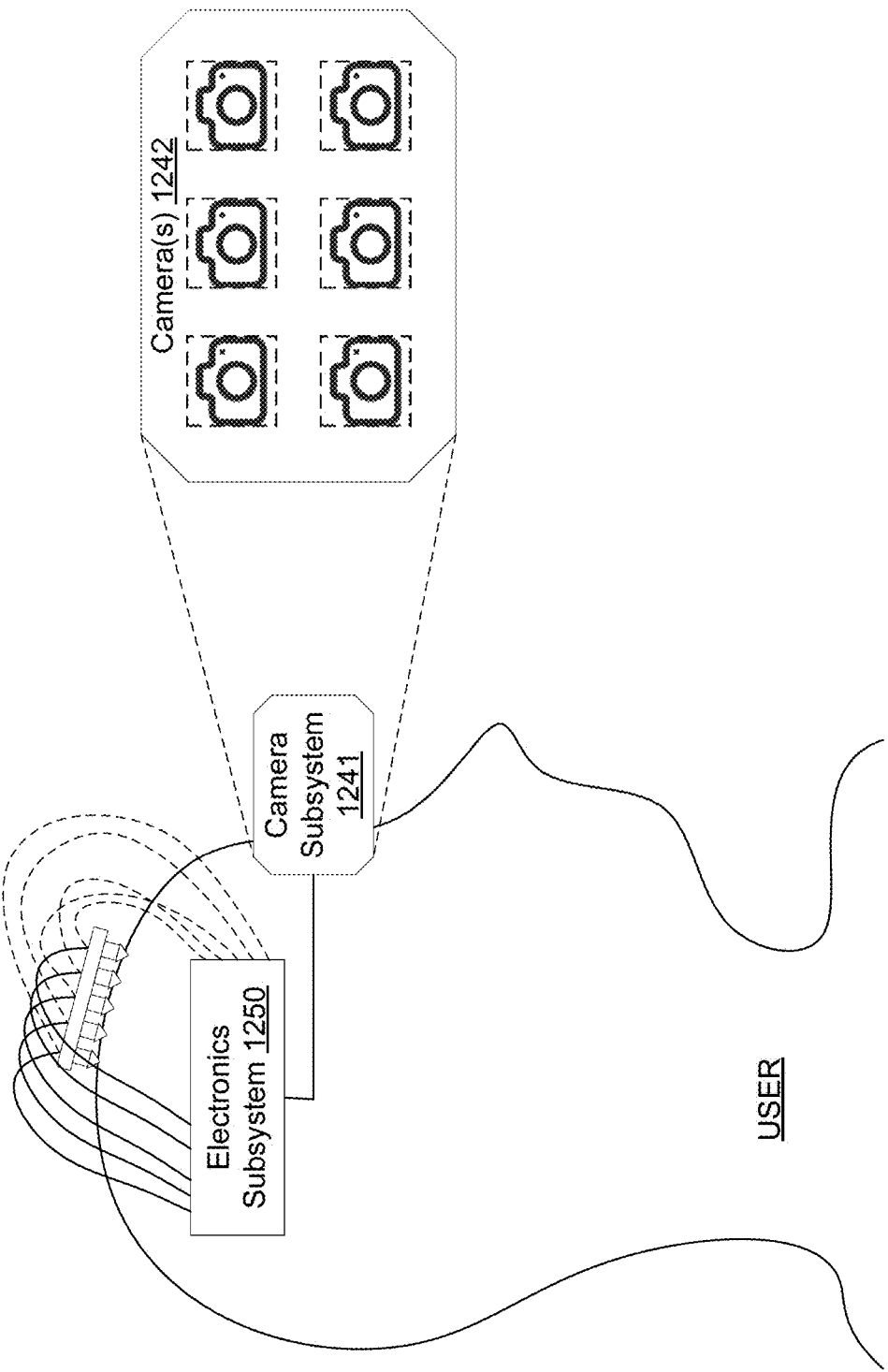
FIG. 12A depicts a schematic of a camera subsystem, in accordance with one or more embodiments.
Figure 12B:
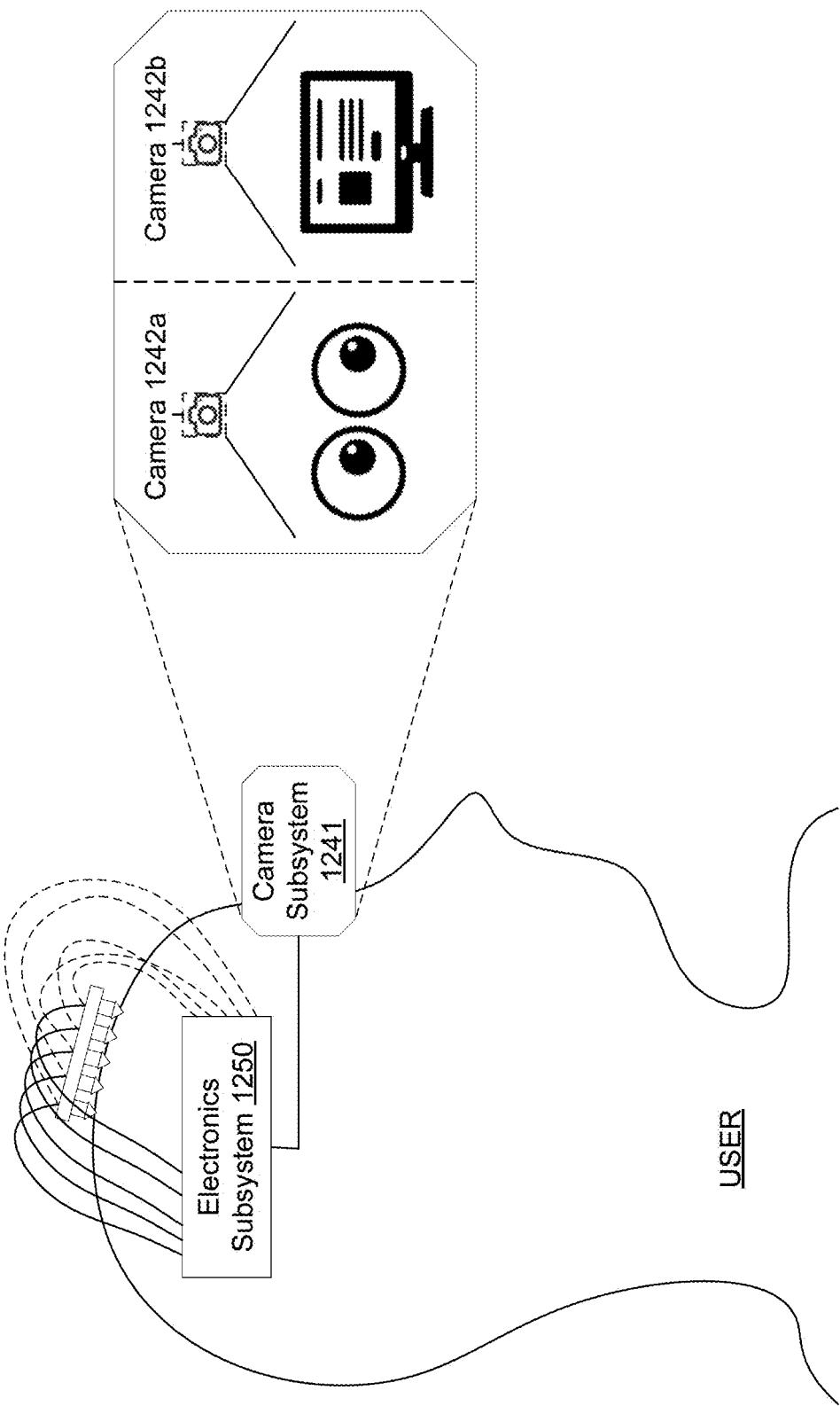
FIG. 12B depicts a schematic of the camera subsystem shown in FIG. 12A.

FIG. 12A depicts a schematic of a camera subsystem 1241, in accordance with one or more embodiments, and FIG. 12B depicts a schematic of the camera subsystem 1241 shown in FIG. 12A. As shown in FIG. 12A, the additional sensors can include one or more cameras 1242 of a camera subsystem 1241, which function to generate image data of the user and/or of an environment of the user. The cameras 1242 utilize light of the visible spectrum, but can additionally or alternatively include sensors that utilize any other portion of the electromagnetic spectrum (e.g., infrared spectrum). The camera subsystem 1241 can use image sensors of the camera(s) 1242 to capture image data and/or video data. In relation to image data and video data, the camera subsystem 1241 can be configured to capture data with sufficiently high resolution to capture features of interest of the user (e.g., pupil position and orientation, facial features, body movements, etc.) and/or of the environment of the user (e.g., states of objects in the environment of the user), where applications of user tracking and environmental tracking are described in more detail below.

In relation to the wearable interface 120 described above, the camera(s) 1242 of the camera subsystem 1241 can be coupled to the wearable interface (and electronics subsystem 1250) shown in FIGS. 12A and 12B, in a manner that orients the camera(s) with a field of view capturing the face (or a portion of the face) of the user, and/or with a field of view capturing an environment of the user (e.g., from a point of view of the user). As such, the camera subsystem 1241 can include a first camera 1242a coupled to (e.g., mounted to, electromechanically coupled to, etc.) a portion of the wearable interface and in an inward-facing orientation to provide a field of view capturing the face of the user, in order to generate eye tracking data (e.g., in relation to coordinates of objects the user looks at, in relation to swell time) of the user and/or facial expressions of the user. The camera subsystem 1241 can also include a second camera 1242b coupled to (e.g., mounted to, electromechanically coupled to, etc.) a portion of the wearable interface and in an outward-facing orientation to provide a field of view capturing the environment of the user, in order to generate image data of objects or environments with which the user is interacting. The camera subsystem 1241 can, however, have more than two cameras coupled to the wearable interface or other portions of the system in another orientation. Additionally or alternatively, the camera(s) can be fixed in position, or can be actuated to adjust field of view.

As indicated above, the camera subsystem 1241 can cooperate with other portions of the system described above, in applications where capturing interactions of the user with the environment of the user can be combined with decoded brain activity of the user in a useful manner. In one such application, the system can monitor, by way of cameras 1242 of the camera subsystem 1241, objects that the user is interacting with in his/her environment by generating and analyzing images of eye motion of the user, head motion of the user, gaze of the user, and/or line-of-sight to objects in the user's environment, decode an intention of the user from brain activity of the user acquired through the detector subsystem described above, and apply the intention as an input to control an operational state of the object. Examples of objects can include electronic content provided at a display (e.g., of a computer, of a wearable device, of an artificial reality system, of a virtual reality system, of an augmented reality system, etc.), electronic content provided at an audio output device, electronic content provided at a haptic feedback device, connected devices (e.g., temperature control devices, light control devices, speakers, etc.), or other objects. Examples of intentions can include desired adjustments to operational states of devices (e.g., turn off device, turn on device, adjust device brightness, adjust device output volume, etc.), desired interactions with electronically-provided content (e.g., select object, select menu item, navigate to another web page, scroll up, scroll down, close window, etc.), desired interactions with a virtual assistant, or any other intentions.

As such, in one specific example, the camera subsystem 1241, in combination with other system outputs, can cooperate to determine that the user is looking at a particular connected light in the user's bedroom, decode a brain activity signal that indicates that the user wants to dim the light, and generate control instructions for dimming the light, all without the user speaking a command or adjusting dimness of the light using a physically-manipulated controller. In another specific example, the camera subsystem 1241, in combination with other system outputs, can cooperate to determine that the user is looking at a selectable button for purchasing an item within an online marketplace, decode a brain activity signal that indicates that the user wants to "click the button", and generate control instructions for selecting the button to purchase the item, all without the user speaking a command or physically clicking the button (e.g., with a mouse).

In relation to the additional sensors 140a shown in FIG. 1A, the system can additionally or alternatively include other sensors and/or biometric sensors for sensing aspects of the user, the user's physiology, and/or the environment of the user. Other sensors can include audio sensors (e.g., microphones), motion/orientation sensors (e.g., accelerometers, gyroscopes, inertial measurement units, etc.), respiration sensors (e.g., plethysmography sensors), cardiovascular sensors (e.g., electrical signal-based cardiovascular sensors, radar-based cardiovascular sensors, force-based cardiovascular sensors, etc.), temperature sensors for monitoring environmental temperature (e.g., ambient temperature) and/or body temperature of the user, other brain activity sensors (e.g., electroencephalography sensors), other electrophysiology sensors (e.g., skin conductance sensors), and/or any other suitable sensors.

Outputs of the additional sensors 140a can be processed with outputs of other system components described above, in order to improve applications where co-processing brain activity information with other sensor-derived information would be beneficial.

4.5 System—Other Electronics

The system can include additional electronics coupled to one or more of the embodiments of the light source subsystem, detector subsystem, additional sensors, network, and/or wearable interface, as described above.

For instance, as shown in FIG. 1A, the system can include a power component 150a that provides power and/or manages power provision to one or more other system components. The power component 150a can include a battery (e.g., rechargeable battery, non-rechargeable battery) electrically coupled to a power management system that maintains desired circuit voltages and/or current draw appropriate for different system components. The power component 150a can be retained within a housing 105a associated with the wearable interface and coupled to the light source subsystem and/or the detector subsystem. As described in relation to other system components below, the housing 105a can house one or more of: the light source subsystem 110a, the detector subsystem 132a, a power component 150a, a computing component 160a, a data link 162a, and additional sensors 140a. The housing 105a can also house at least a portion of the interface 120a that is head-mountable for positioning signal transmission components at the head region of a user. The housing 105a can be head-mounted or can be coupled to the user in another manner. The housing can be composed of a polymer material and/or any other suitable materials.

As shown in FIG. 1A, the system can also include a computing component 160a that functions to coordinate light transmission from the light source subsystem and/or operation states of the detector subsystem (e.g., in relation to emission from the light source subsystem). The computing component 150a can thus include architecture storing instructions in non-transitory computer readable media for implementing portions of methods described, controlling operation states of the light source subsystem, the detector subsystem, and/or additional sensors, monitoring states of components coupled to the computing component 160a, storing data in memory, coordinating data transfer (e.g., in relation to the data link described below), and/or performing any other suitable computing function of the system. The computing component 160a can additionally or alternatively include signal conditioning elements (e.g., amplifiers, filters, analog-to-digital converters, digital-to-analog converters, etc.) for processing signal outputs of sensors of the system.

As shown in FIG. 1A, the system can also include a data link 162a coupled to the computing component 160, for handling data transfer between electronics of the wearable system components and the network 170a. The data link 165a can provide a wired and/or wireless (e.g., WiFi, Bluetooth LE, etc.) interface with the network or other external systems.

5. Method—Neural Decoding Process with Co-Learning

Figure 13:
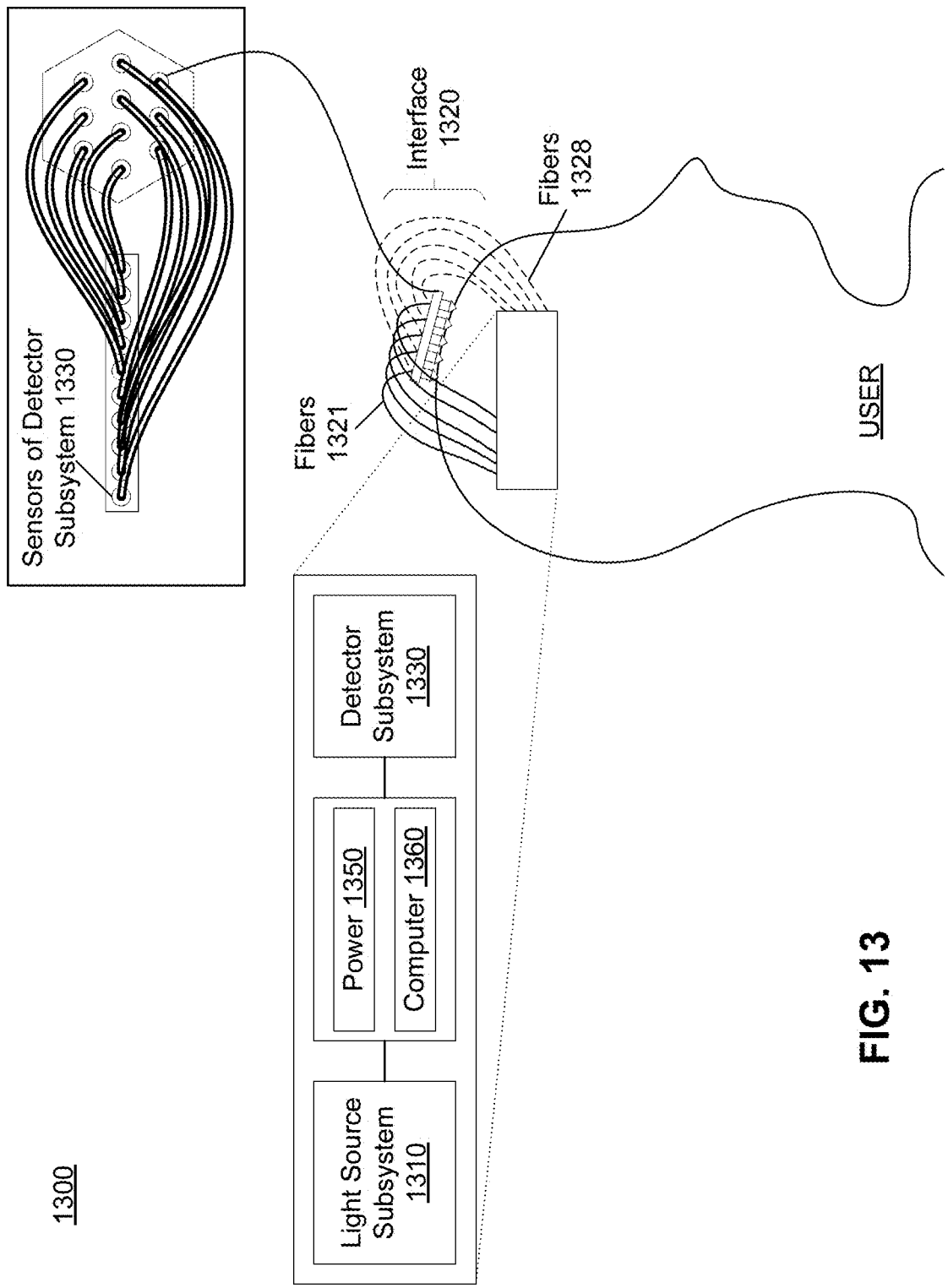
FIG. 13 depicts a schematic of an embodiment of a system, with computing components, for implementing a neural decoding process.

FIG. 13 depicts a schematic of an embodiment of a system with computing components for implementing a neural decoding process. The system shown in FIG. 13 is an embodiment of the system shown in FIG. 1B, and includes a light source subsystem 1310, an interface 1320 transmitting light from the light source subsystem 1310 to a head region of a user, and a detector subsystem 1330 coupled to the interface 1320 and configured to receive light signals from the head region of the user. The light source subsystem 1310 and the detector subsystem 130 are coupled to a power component 1350 and a computing component 1360, which processes and decodes neural stream signals for delivery of feedback to a user as a closed-loop system. The system shown in FIG. 13 can be used to implement the methods described below, in relation to receiving and processing neural signal streams including, at least partially, signals derived from light transmitted from the head region of the user. In particular, the system can apply optical tomography (DOT) to generate blood oxygen level dependent (BOLD) signals, which can be decoded using a trained neural decoding model to determine user actions, as described below.

Figure 14A:
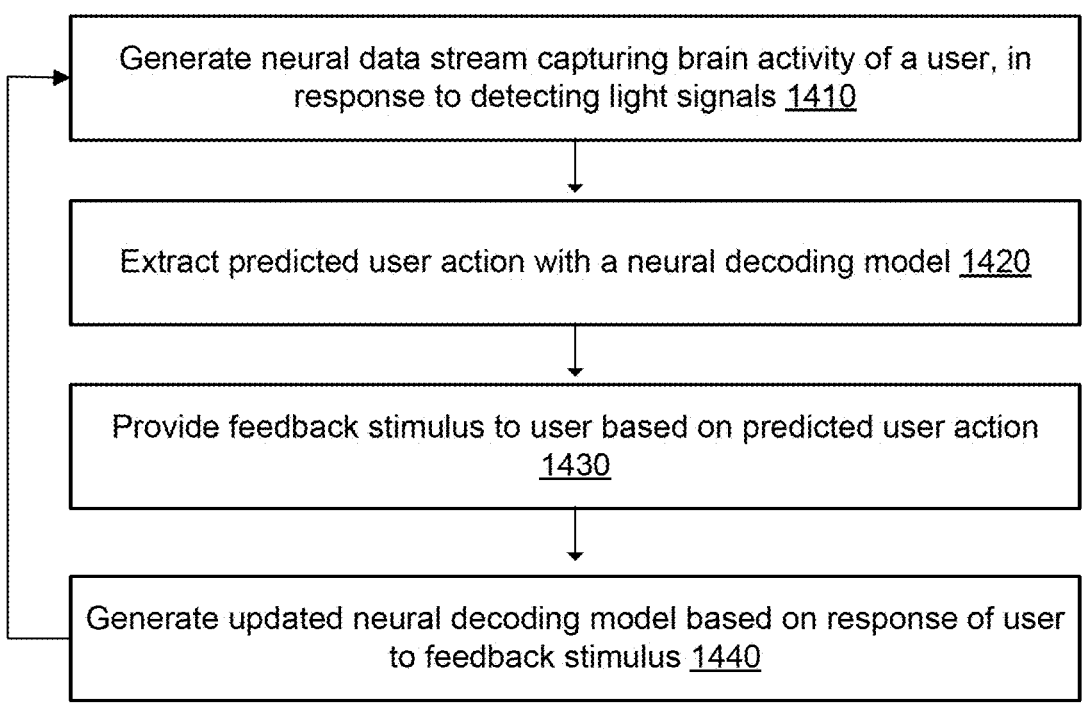
FIG. 14A depicts a flow chart of a method for neural decoding, in accordance with one or more embodiments.
Figure 14B:
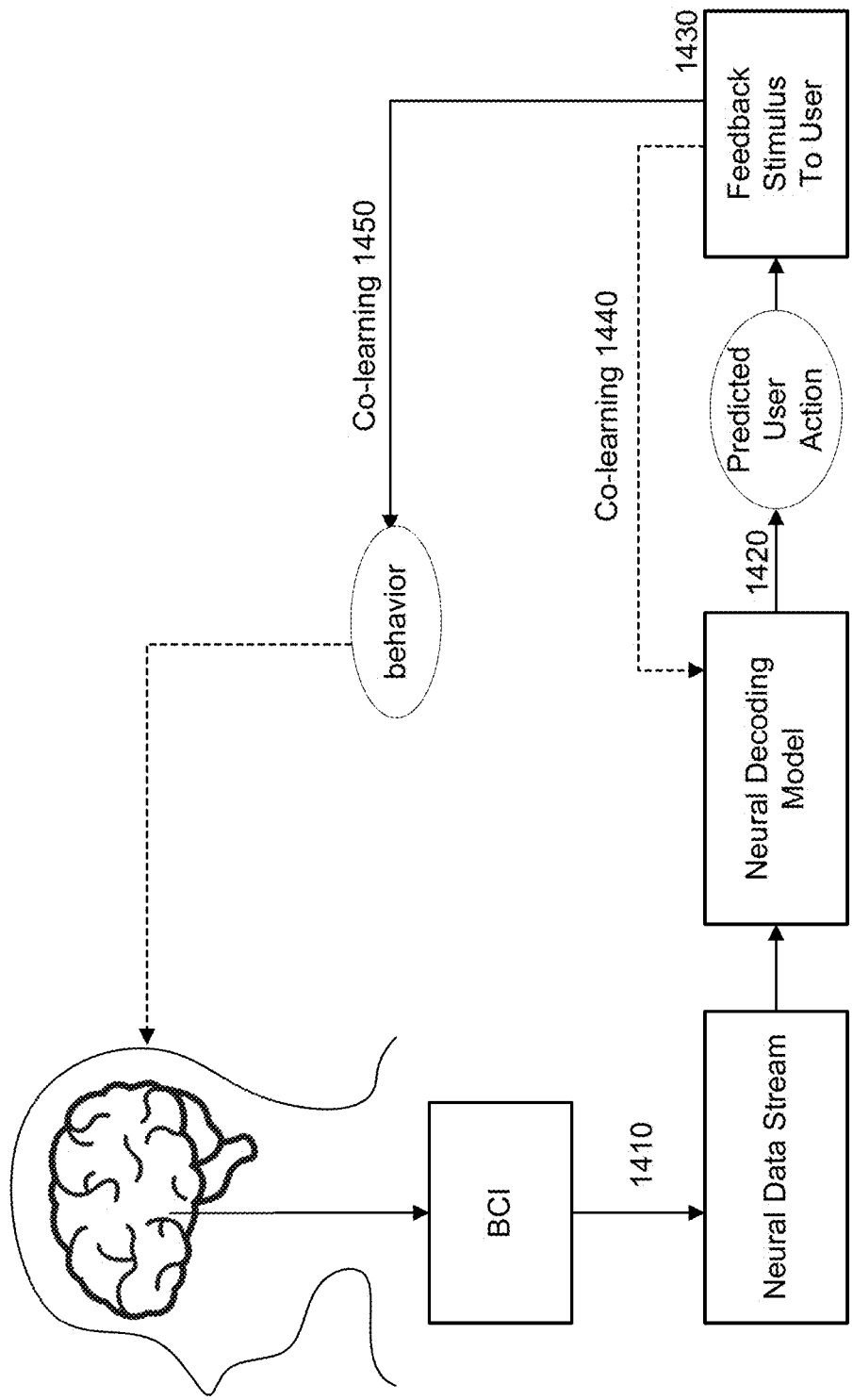
FIG. 14B depicts a flow diagram of an embodiment of the method for neural decoding shown in FIG. 14A.

FIG. 14A depicts a flow chart of a method 1400 for neural decoding, in accordance with one or more embodiments. FIG. 14B depicts a flow diagram of an embodiment of the method for neural decoding shown in FIG. 14A. As shown in FIGS. 14A and 14B, the system (e.g., light transmission, light detection, and computing components) generates 1410 a neural data stream capturing brain activity user in response to detecting a set of light signals from a head region of a user as the user interacts with an object in an environment. The system extracts 1420 a predicted user action upon processing the neural data stream with a neural decoding model, where the predicted user action can be actual (e.g., actual speech) or imagined (e.g., thought), as described in more detail below. The system then provides 1430 a feedback stimulus to the user based upon the predicted user action, and generates an updated neural decoding model based upon a response of the user to the feedback stimulus 1440. The system also implements one or more co-learning processes 1440, 1450 for improvement of the neural decoding model and/or behavior of the user. As such, the method 1400 can provide a closed loop process whereby the neural decoding model is updated and trained as the user interacts with content or other stimuli, and provides additional light-derived signals that capture brain activity.

The method 1400 functions to rapidly (e.g., in real time or near real time) decode light-derived signals to extract predicted user actions or intents (e.g., commands) in relation to interactions with objects (e.g., virtual objects, physical objects), such that the user can manipulate the objects or otherwise receive assistance without manually interacting with an input device (e.g., touch input device, audio input device, etc.). The method 1400 thus provides a neural decoding process with the neural stream signal as an input, and provides feedback to the user, where the feedback is used to train the neural decoding algorithm and user behavior. The neural signals can be blood oxygenation level dependent (BOLD) signals associated with activation of different articulators of the motor cortex, and signals can characterize both actual and imagined motor cortex-related behaviors. With training of the decoding algorithm, rapid calibration of the system for new users can additionally be achieved.

5.1 Method—Generating Data

As shown in FIGS. 14A and 14B, the system (e.g., light transmission, light detection, and computing components) generates 1410 a neural data stream capturing brain activity of the user as the user interacts with an object, which functions to generate source data that can be processed with the neural decoding model to decode cognition through a non-traditional method. As noted above, the neural data stream is derived from input light signals that are provided to the user's head and output light signals that are captured after passing through the user's head, where the output signals carry information about the level of oxygen present in blood of the user, associated with different regions. As such, the signals associated with the neural data stream are a type of blood oxygen-level dependent (BOLD) signal that carries hemodynamic response information. In use, signals generated can be evaluated for reliability, such that only reliable signals are passed by the computing subsystem through downstream processing steps to generate predicted user actions. Reliability can be evaluated based upon consistency in signal characteristics (e.g., variances around a mean signal characteristic).

As described above in relation to the detector subsystem, in generating the neural data stream, the system can transform input signals from a detector-associated space (e.g., in relation to fiber optics coupled to an array of detector pixels) to a brain region-associated space (e.g., in relation to brain regions associated with the input signals). Also described above in relation to embodiments of the detector subsystem, signals of the neural data stream that are derived from unsaturated and saturated grouped pixel units that receive light from distinct head regions, where, for saturated grouped pixel units, features can be extracted from saturated central regions and/or unsaturated edge regions. The signals derived from saturated portions can include information related to positions of boundaries between a saturated central region of a grouped pixel unit and unsaturated edge regions of the grouped pixel unit (indicative of total power), diameter of a saturated central region of a grouped pixel unit, projected area of a saturated central region of a grouped pixel unit, or any other suitable shape-related features associated with the saturated central region. Features related to unsaturated edge regions of the grouped pixel units can include positions of boundaries between unsaturated edge regions of the grouped pixel unit, slope related features (e.g., rates of decay) of a heel portion of an unsaturated edge region, features related to integrated areas under an intensity curve corresponding to unsaturated edge regions, or any other suitable shape-related features associated with the unsaturated edge region. While signal characteristics associated with intensity are described above, signal characteristics that can be derived from the generated light signals can include features of any other suitable light-related parameter.

Also described above in relation to the detector subsystem, the system can generate signals of the neural data stream associated with multiple light exposure levels (e.g., short and long exposure levels), different light power settings (e.g., a low power setting, a high power setting), and/or different light parameter settings.

In relation to the detector subsystem described above, the neural data stream includes data from separate head regions (e.g., separate head regions associated with a single cortex, separate head regions associated with multiple cortices) of the user. In one embodiment, the neural data stream includes light data from different head regions, where signals from the different head regions map to a set of motor cortex articulators associated with articulation of different speech components. Articulation can be actual or imagined, such that the signals can carry information associated with actual or imagined speech. Furthermore, with repeated iterations of the method 1400, the computing subsystem can generate a template that refines mapping between the detector subsystem components and specific brain anatomy of the user(s) associated with the method 1400. Over time, aggregation and processing of large amounts of data from the user(s) can be used to provide rapid calibration of system components and system response for the user(s) and/or new users.

Figure 14C:
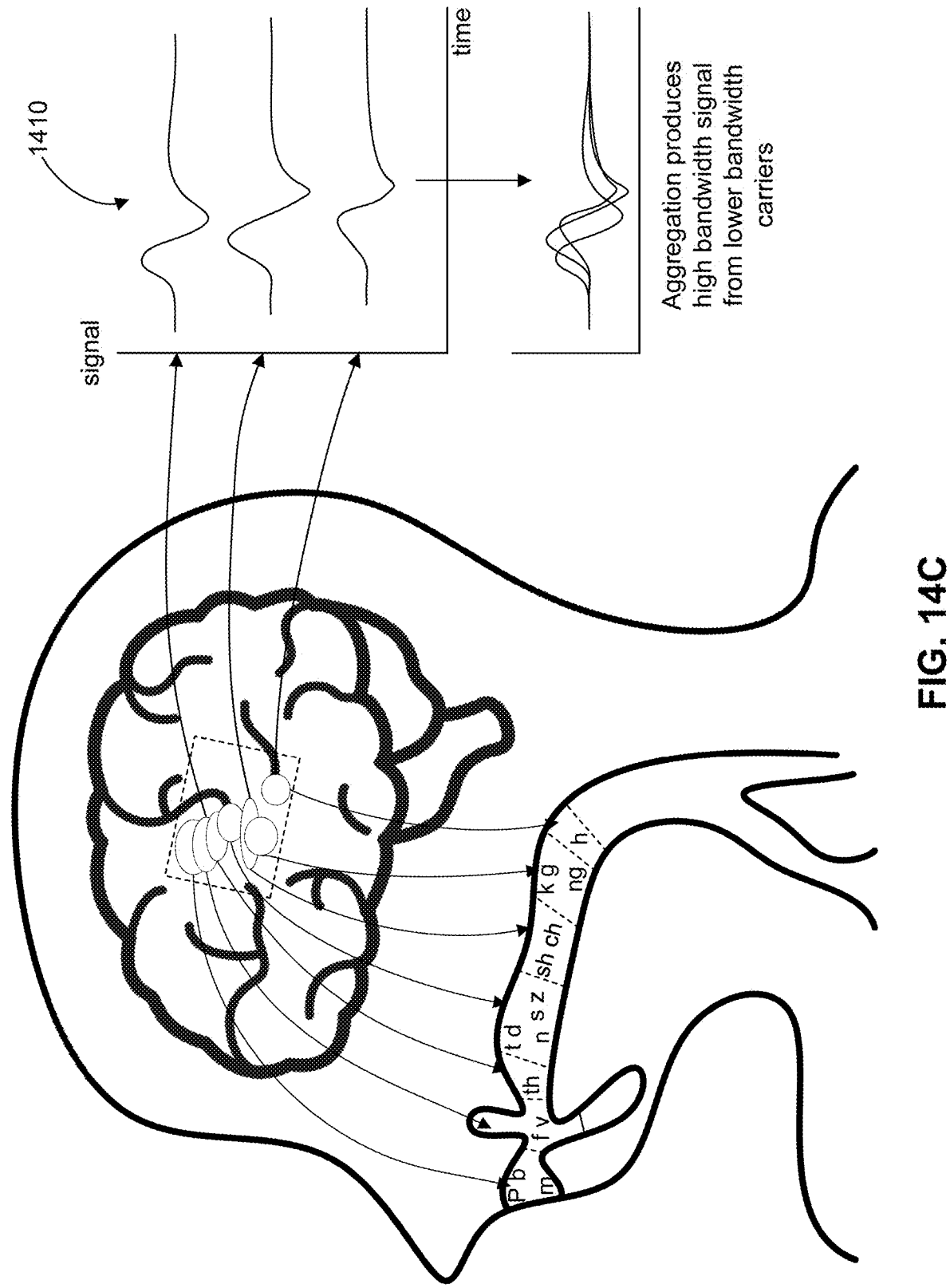
FIG. 14C depicts a schematic of a neural data stream capturing information associated with different articulators, in relation to an embodiment of the method shown in FIG. 14A.

FIG. 14C depicts a schematic of a neural data stream capturing information associated with different articulators, in relation to an embodiment of the method shown in FIG. 14A. In the schematic shown in FIG. 14C, the neural data stream contains information from different brain/head regions that map to different articulators, where the different articulators are associated with different speech components (e.g., phonemes). In more detail, the neural data stream captures data associated with a first set of light signals corresponding to a first articulator, where the first articulator is a labial articulator associated with the phonemes "p", "b", and "m". The neural data stream also captures data associated with a second set of light signals corresponding to a second articulator, where the second articulator is a labiodental articulator associated with the phonemes "f" and "v". The neural data stream also captures data associated with a third set of light signals corresponding to a third articulator, where the third articulator is a dental articulator associated with the phoneme "th". The neural data stream also captures data associated with a fourth set of light signals corresponding to a fourth articulator, where the fourth articulator is an alveolar articulator associated with the phonemes "t", "d", "n", "s", and "z". The neural data stream also captures data associated with a fifth set of light signals corresponding to a fifth articulator, where the fifth articulator is a postalveolar articulator associated with the phonemes "sh" and "ch". The neural data stream also captures data associated with a sixth set of light signals corresponding to a sixth articulator, where the sixth articulator is a velar articulator associated with the phonemes "k", "g", and "ng". The neural data stream also captures data associated with a seventh set of light signals corresponding to a seventh articulator, where the seventh articulator is a glottal articulator associated with the phoneme "h". In alternative embodiments, however, the neural data stream can additionally or alternatively capture data associated with light signals corresponding to different articulators and/or different speech components. In relation to generation of the neural data stream, the detector subsystem can be configured to separate detector subregions associated with different articulators, in order to increase distinction between signals associated with different articulators.

In relation to signals of the neural data stream shown in FIG. 14C, the signals associated with different articulators can be aggregated and processed, as described in downstream portions of the method 1400, in order to generate higher bandwidth signals from lower bandwidth carriers associated with articulator-specific signals received at different time points. As such, sequences of activation of different articulators associated with actual or imagined speech can generate low bandwidth carrier signals that can be processed, in relation to temporal and spatial factors, to produce a higher bandwidth signal that can be decoded.

In other embodiments, the system can generate a neural data stream using other techniques including any or more of: functional magnetic resonance imaging (fMRI), other forms of blood-oxygen-level dependent (BOLD) contrast imaging, near-infrared spectroscopy (NIRS), magnetoencephalography (MEG), electrocorticography (ECoG), electroencephalography (EEG), positron emission tomography, nuclear magnetic resonance (NMR) spectroscopy, single-photon emission computed tomography.

5.2 Method—Extracting Predicted User Action

Figure 14D:
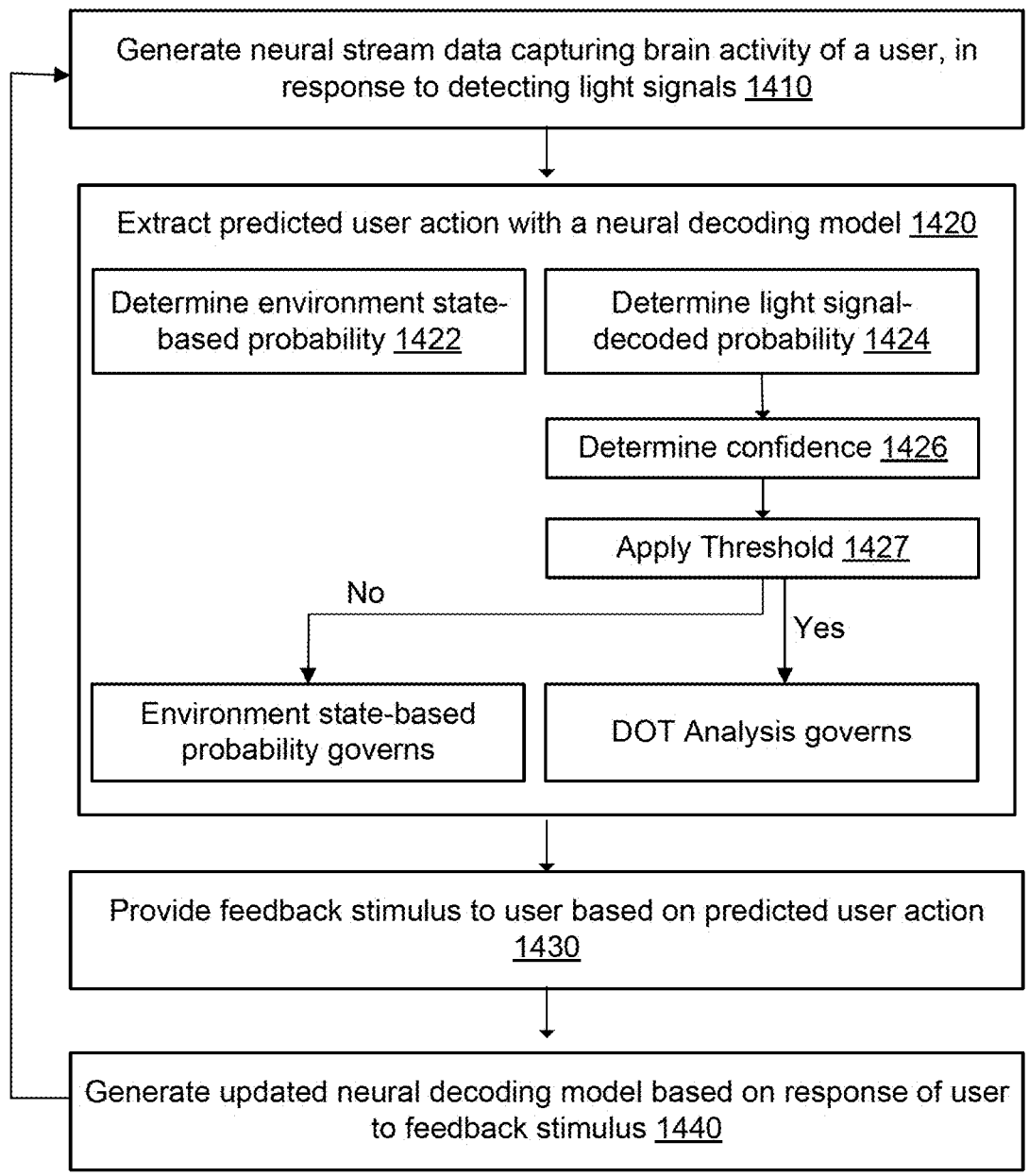
FIG. 14D depicts a process flow of an embodiment of the method shown in FIG. 14A.

FIG. 14D depicts a flow chart of a portion of the method for neural decoding shown in FIG. 14A. As shown in FIG. 14D, the system (e.g., computing components) extracts 1420 a predicted user action upon processing the neural data stream with a neural decoding model, which functions to transform captured input signals associated with the neural data stream into decoded information that can be used to trigger responses (e.g., by environmental objects) that benefit the user in some manner. The predicted user action, as described above, can include a prediction of actual or imagined speech of the user, where the speech is associated with commands provided by the user to manipulate one or more objects in the environment of the user. The objects can be associated with a virtual or a real environment. For instance, the object can be a player or other entity in a virtual game environment, where the predicted user action is an action that manipulates behavior (e.g., movement) of the player or entity within the virtual game environment. In another example, the object can be a digital object associated with a virtual assistant, such that the predicted user action is an action that commands the virtual assistant to perform a task (e.g., in relation to scheduling, in relation to device operation state manipulation, in relation to executing communications with entities associated with the user, etc.). In another example, the object can be a connected object (e.g., a smart home light, smart home thermostat, smart home speaker, smart home appliance, other smart home device, etc.), such that the predicted user action is an action that affects operation of the connected object, through provision of control instructions to the connected object. In alternative embodiments, however, the predicted user action can be an action associated with different motor cortex functions (e.g., actual or imagined movement of another part of the body), different cognitive functions, different cognitive states (affective states, etc.). The action can, however, be another suitable action.

In relation to extracting predicted user actions, the system (e.g., computing components of the system) can implement a neural decoding model that decodes the probability of a predicted action based upon environment/object state and an analysis of information from the neural data stream. As such, the system, as shown in FIG. 14D, can perform decoding by determining 1422 an empirical probability of an action due to state of the object and/or environment associated with the object, and by determining 1424 a light signal-decoded probability as determined from the neural data stream. In one embodiment, the probability function can be assumed to have the shape: p(predicted user action|environment state, neural data)=softmax[$\alpha$*Q(predicted user action|environment state)+$\beta$*L(predicted user action neural data)], where p is the probability of the predicted user action. Q is determined from an analysis of probability of a given action from a set of candidate options based upon the environment or object state. L is a negative log-likelihood given by an estimator (e.g., neural network model) that is trained based upon incoming neural data from one or more users. The parameters $\alpha$ and $\beta$ are free hyperparameters.

In an example associated with a gaming environment, where the goal is to navigate a grid to drive a character toward a prize positioned within the grid, Q is determined by policy iteration over the available positions on the grid. In more detail, Q in this example is the negative of the distance from the position of the character to the position of the prize, where the distance can be measured by Dijkstra's algorithm or another distance-determining algorithm. In different environments (e.g., other virtual or real environments) with different objects, however, Q can be used to determine a probability of an action based on environment state with another process.

In an example where the predicted user action is associated with actual or imagined speech commands, the neural decoding model can determine L upon receiving and aggregating sequences of signals associated with the speech articulators, in order to form single or multi-consonant words that represent different commands. As such, the neural decoding model can transform the neural data stream into a set of speech components mapped to a set of motor cortex articulators associated with the head region or, can transform a sequence of activated motor cortex articulators, captured in the set of light signals of the neural data stream, into one or more phoneme chains representative of the commands. Based on the set of articulators from which signals are able to be captured by the detector subsystem, the phoneme chains can be literally translated into the commands (e.g., phoneme chains that form directional words). Additionally or alternatively, the phoneme chains can be trained representations of a spoken version of the commands. For instance, a phoneme chain of "h" "th" "m" detected in the neural data stream can translate to "hotham", a phoneme chain of "v" "d" "k" detected in the neural data stream can translate to "vadok", a phoneme chain of "p" "ch" "th" detected in the neural data stream can translate to "poochoth", and a phoneme chain of "k" "v" "n" detected in the neural data stream can translate to "kevin", where the representative words "hotham", "vadok", "poochoth", and "kevin" map to different commands (e.g., commands that move a character in different directions, such as left, right, up, and down, in a virtual environment).

Also shown in FIG. 14D, implementation of the neural decoding model can include modulating which components (e.g., an environment state-based component, a neural data stream-based component) govern the output of the model. In more detail, as shown in FIG. 14C, the computing subsystem can determine 1422 an environment state-based probability associated with the predicted user action and determine 1424 a light signal-decoded probability associated with the user action. The computing subsystem can also determine 1426 a value of a confidence parameter associated with the light signal-decoded probability, and compare 1427 the value of the confidence parameter to a threshold condition. Then, if the threshold condition is satisfied, the output of the neural decoding model can be based upon the light signal-decoded data (e.g., as determined using a diffuse optical tomography analysis). However, if the threshold condition is not satisfied, the output of the neural decoding model can be based upon the environment state-based probability analysis. Alternatively, the computing subsystem can implement a weighting function that weighs the confidences in each of the environment state-based analyses and the light-signal decoded analyses, and provides an output that combines the weighted probability components as an aggregated output (e.g., based on convex combination, based on another combination algorithm).

As such, without knowledge by the user, the computing subsystem can ensure that the neural decoding model 1420 outputs a predicted user action, even if the confidence in the analysis of the action captured in the neural data stream is low, by using an empirical probability determined from the environment state. Furthermore, the computing subsystem can implement training data from situations where the predicted user action is known, in order to increase the accuracy of the light-decoded probabilities. Then, as the confidence in the light signal-decoded probability based on analysis of the neural data stream increases, the computing subsystem can primarily output predicted user actions based on analysis of the neural data stream, as the accuracy in decoding light signals of the neural data stream increases.

Figure 14E:
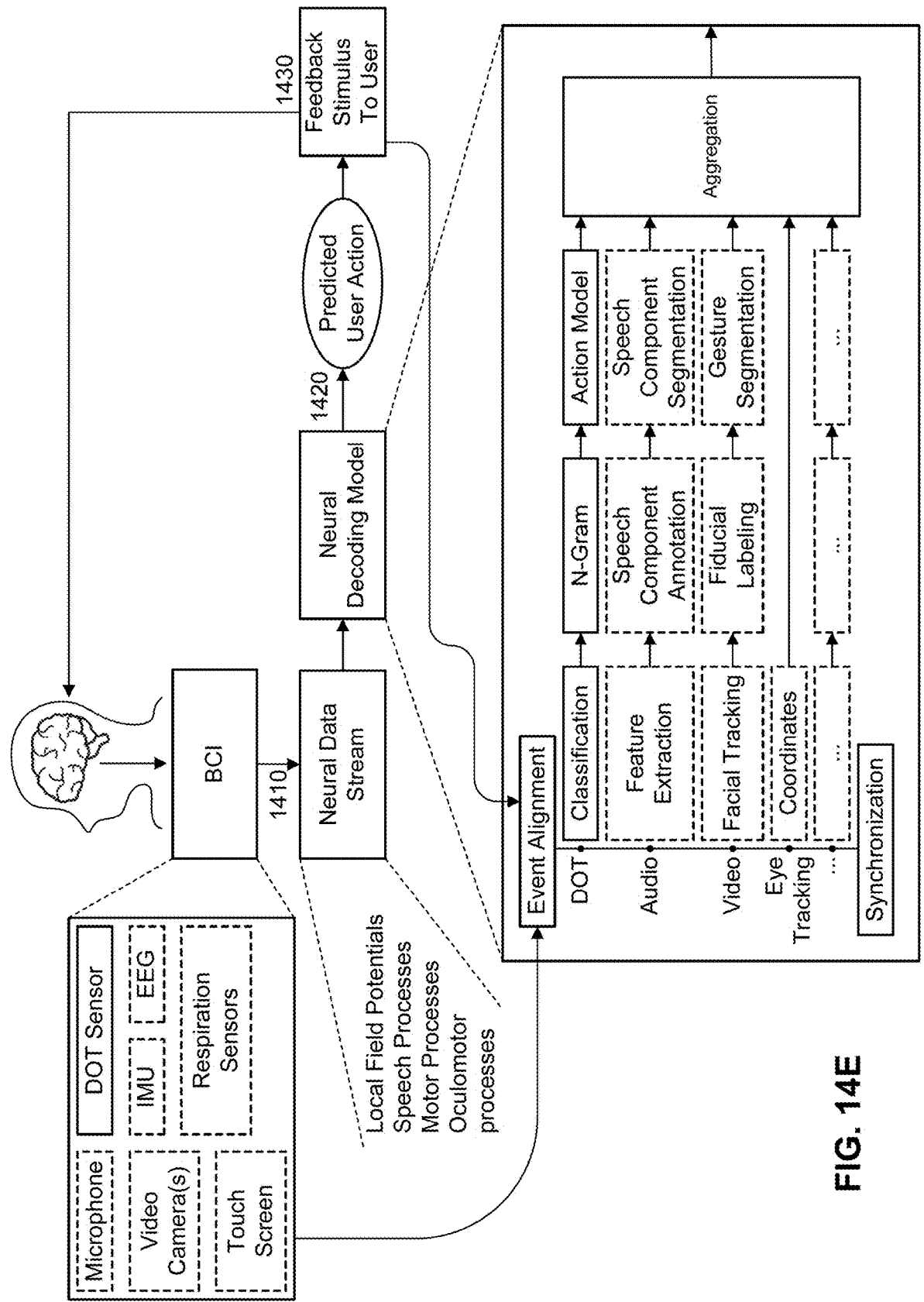
FIG. 14E depicts an expanded view of a portion of the process flow shown in FIG. 14D.

FIG. 14E depicts an expanded view of a portion of the process flow shown in FIG. 14D, in relation to implementation of the neural decoding model as applied to input signals derived from sensors associated with the brain computer interface. As shown, input signals can be associated with hemodynamic responses captured in light signals. Input signals can additionally or alternatively include local field potentials, signals capturing speech processes (actual or imagined speech processes), signals capturing oculomotor processes, signals capturing other motor processes, other biometric data (e.g., associated with respiration, etc.) and other suitable input signals, based on sensor outputs of the BCI. In particular, an embodiment of the detector subsystem can generate light signals associated with hemodynamic response in relation to different articulators, as described above. Additionally, one or more microphones can generate audio signals (e.g., capturing speech information) that can supplement data used to generate the predicted user action. Additionally, one or more video cameras can generate video data associated with the user's face or eyes and/or an environment of the user that can supplement data used to generate the predicted user action. Additionally, one or more touch sensors can generate signals indicative of motor skill activities of the user that can supplement data used to generate the predicted user action. Additionally, one or more motion sensors (e.g., of an inertial measurement unit) can generate signals indicative of motion of the user that can supplement data used to generate the predicted user action. Additionally, other brain activity sensors (e.g., electrodes for electroencephalography, etc.) can generate signals from electrical potentials that can supplement data used to generate the predicted user action. Additionally, other biometric sensors (e.g., respiration sensors, cardiovascular parameter sensors, etc.) can generate signals that can supplement data used to generate the predicted user action.

In relation to processing of the neural data stream, input light signals derived from one or more embodiments of the detector subsystem described above can be classified by the computing subsystem hosting the neural decoding model into groups associated with different articulators (e.g., different articulators associated with different speech components, an example of which is shown in FIG. 14C). Then, outputs of the classification can be assembled (e.g., into n-grams), based upon temporal factors or other factors. The computing subsystem hosting the neural decoding model can then process the assembled information with an action prediction model. In one embodiment, the computing subsystem can transform signals associated with a sequence of activated motor cortex articulators (e.g., as captured in a set of light signals) into a phoneme chain representative of a command intended to be executed by the user.

If including analysis of audio signals in the neural decoding model, the computing subsystem hosting the neural decoding model can also extract features of the audio signals, determine and annotate speech components or other audio components from the audio signals, and perform a segmentation operation to determine boundaries between individual speech components, in relation to a user action. If including analysis of video signals in the neural decoding model, the computing subsystem hosting the neural decoding model can also implement facial feature tracking algorithms, with fiducial labeling and gesture segmentation models, in relation to detecting a user action. The computing subsystem can additionally or alternatively process video signals in order to track motions of the eye(s) of the user, in order to determine coordinates of objects that the user is looking at and/or dwell time, in relation to a user action. The neural decoding model can additionally or alternatively accept other input signals, which can be aggregated by architecture of the neural decoding model to combine features into an output of a predicted user action (e.g., with a confidence score).

In relation to the neural decoding model, the computing subsystem can include architecture for synchronization of input signals associated with the same or different sensors, in relation to an event (e.g., an environment state, an object state, a stimulus, a feedback stimulus provided based on a predicted user action, as described in more detail below, etc.). In order to synchronize input signals, the computing subsystem can include architecture for signal registration (e.g., based upon temporal signatures within different signals, based upon interpolation of signals with different associated sampling rates, etc.), to a desired degree (e.g., with millisecond alignment, with microsecond alignment, etc.). As such, the computing subsystem implements the neural decoding model to extract predicted user actions contemporaneously (e.g., within a time threshold to) a time point associated with an event, such as a state of an environment or object associated with the user.

5.3 Method—Providing Feedback Stimulus

Figure 14F:
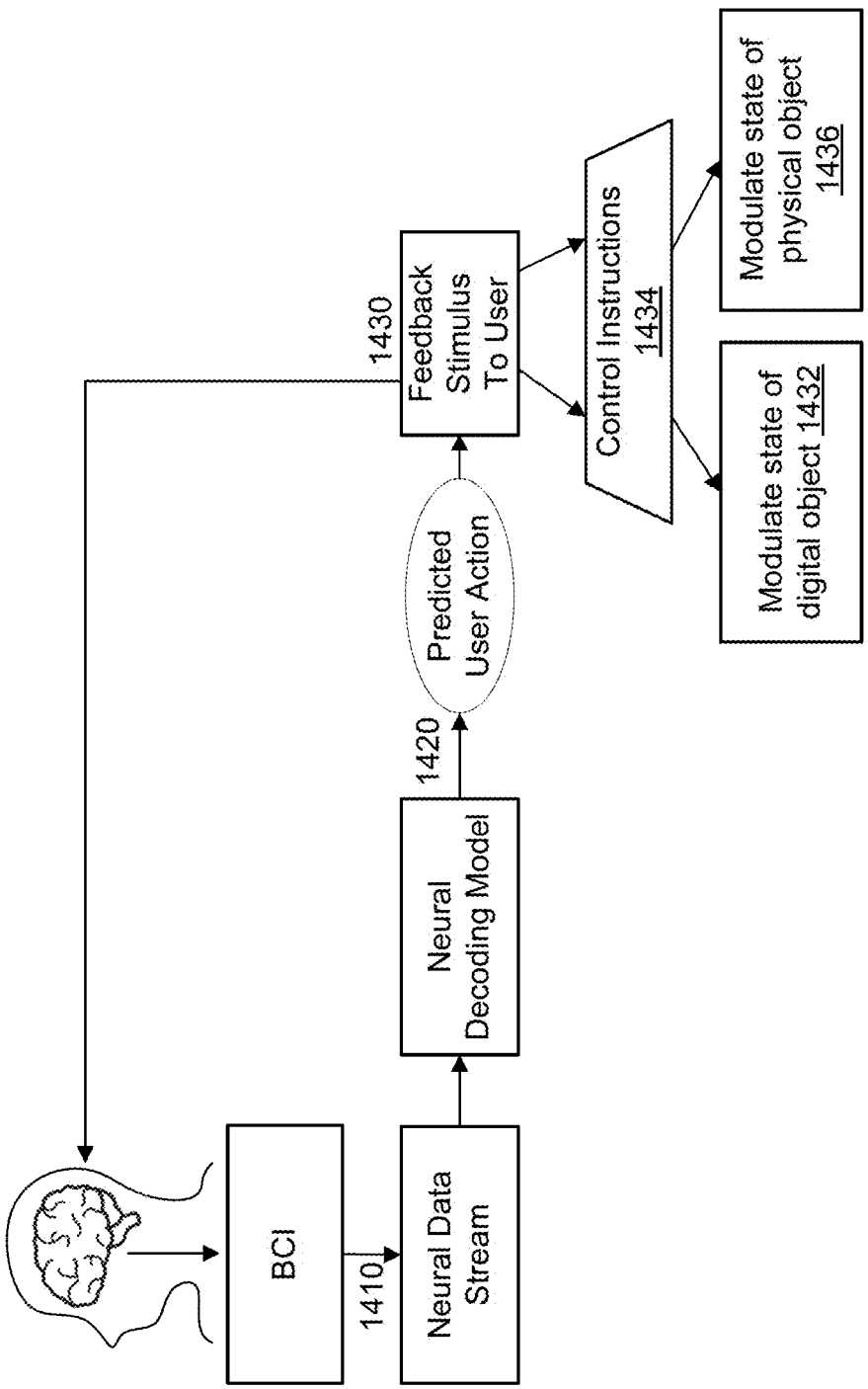
FIG. 14F depicts an expanded view of a portion of the process flow shown in FIG. 14D.

As shown in FIGS. 14A, 14D, and 14F, where FIG. 14F depicts an expanded view of a portion of the process flow shown in FIG. 14B, the computing subsystem provides 1430 a feedback stimulus to the user based on the predicted user action output by the neural decoding model. The feedback stimulus can be a representation of the predicted user action output by the neural decoding model, in text or other visual format, in audio format, and/or in haptic format. For instance, if the predicted user action is associated with a command (e.g., a command to manipulate an object) or request, the feedback stimulus can be a textual representation of the command or request, or a symbolic representation of the command or request. In a specific example, if the command is an indication by the user that the user wants to move an object in a direction, the feedback stimulus can be a rendered text description of the direction or a rendered arrow depicting the direction, where the computing subsystem generates instructions for rendering the feedback stimulus at a display. In another specific example, if the command is an indication by the user that the user wants to move an object in a direction, the feedback stimulus can be an audio output that states the direction in speech, where the computing subsystem generates instructions for transmitting audio through a speaker of a device associated with the user. The representation of the command, provided to the user as the feedback stimulus, can be validated by the user (e.g., the user can indicate that the predicted user action is correct, based upon the feedback stimulus), as a transitional step to execution of the command or request by the computing subsystem or other device. Additionally, as described below, the representation of the command, provided to the user as the feedback stimulus, can be used in a co-learning process in order to train the user's behavior (e.g., to provide feedback to the user so that the user can tune his/her behaviors to provide signals that are more easily decoded), such that training of the neural decoding model occurs in coordination with training of user behaviors to increase the accuracy of the neural decoding model.

In providing the feedback stimulus, the computing subsystem can also generate instructions for execution of a command or request by the user, in relation to modulation of a state of a digital object 1432 or a physical object 1436, with generation 1434 of control instructions in a computer-readable medium for object modulation, several examples of which are described below.

In the context of a game architected in a digital platform, the feedback stimulus can include direct manipulation of a user's character in the game, in terms of motion, behavior, or another action performable by the user's character. In a specific example, execution of the command can include moving the user's character in the game environment, in direct response to the predicted user action being associated with a direction in which the user intends the character to move. In the context of a game architected in a digital platform, the feedback stimulus can include direct manipulation of a game environment, in terms of adjustable parameters in the virtual environment.

In the context of a virtual assistant platform, the feedback stimulus can include generation of control instructions for the virtual assistant to navigate and/or manipulate systems in order to perform a task for the user. For instance, the computing subsystem can generate control instructions that instruct the virtual assistant to execute communication (e.g., in a text message, in an audio message, etc.) with an entity associated with the user, to generate a reminder, to perform a calendar-related task, or to perform another task.

In the context of a virtual environment, with menus or other selectable objects, the feedback stimulus can include execution of instructions for selection of the object or navigation of a menu, based upon the predicted user action.

In the context of connected devices physically associated with a real environment of the user, the feedback stimulus can include manipulation of operation states of the connected device(s). In examples, the connected device(s) can include one or more of: temperature control devices, light control devices, speakers, locks, appliances, and other connected devices. In providing the feedback stimulus, the computing subsystem can generate control instructions for adjusting operational states of devices (e.g., turn off device, turn on device, transition device to idle, adjust device brightness, adjust device output color, adjust device output volume, adjust device sound output profile, adjust microphone operation state, adjust temperature output, adjust lock state, adjust appliance operation state, etc.)

In other contexts, the feedback stimulus may not be related to a command or request. For instance, the predicted user action can be a subconscious cognitive state or affective state, and the computing subsystem can generate and/or execute instructions for manipulation of an object or environment based upon the subconscious cognitive state or affective state.

5.4 Method—Co-Learning

As shown in FIGS. 14A and 14B and described above, the system also implements one or more co-learning processes 1440, 1450 for improvement of the neural decoding model and/or behavior of the user. In relation to the co-learning processes, the computing subsystem implementing the method 1400 provides a closed loop process whereby the neural decoding model is updated and trained as the user interacts with content or other stimuli, and provides additional light-derived signals that capture brain activity. Additionally, the feedback stimuli provided to the user produces a behavior by the user and can be used to train the user in relation to adjusting responses to the environment in a manner that is more efficiently decoded by the neural decoding model. As such, the method 1400 can implement computing architecture that inputs an output derived from the feedback stimulus (e.g., verification that the feedback stimulus was appropriate in relation to a user action) back into the neural decoding model, in order to refine the neural decoding model. In relation to a closed-loop system, the computing subsystem can, based upon a behavior of the user in response to the feedback stimulus, process additional signals from the user to generate additional predicted user actions (with refinement of the neural decoding model). Then, based upon the additional predicted user actions, the computing subsystem can provide additional feedback stimuli to the user, derivatives of which and/or responses to which can be used to further refine the neural decoding model.

6. Conclusion

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A system comprising:
a housing;
a light source subsystem comprising an array of emitters contained within the housing;
a head-mountable interface retained in position by the housing, and physically and optically coupled to the array of emitters by a first set of optical fibers, the head-mountable interface retaining ends of the first set of optical fibers in position at a multidimensional region of interest;
a detector subsystem contained within the housing and comprising an array of pixels arranged linearly along an axis as a set of grouped pixel units, the set of grouped pixel units optically coupled to the head-mountable interface by a second set of optical fibers and configured to receive light signals from the multidimensional region of interest, wherein the set of grouped pixel units omit buffer regions separating adjacent grouped pixel units in the set of grouped pixel units; and
an electronics subsystem contained within the housing and electrically coupled to the light source subsystem and the detector subsystem.

2. The system of claim 1, wherein the light source subsystem comprises an array of vertical cavity surface emitting laser (VCSEL) elements configured to emit red spectrum and infrared spectrum light.

3. The system of claim 2, wherein each VCSEL element in the array of VCSEL elements is physically separated from other VCSEL elements of the array of VCSEL elements and is individually wired to an electronics substrate of the electronics subsystem.

4. The system of claim 2, further comprising an optically opaque medium retained between individual optical fibers of the first set of optical fibers.

5. The system of claim 1, wherein the electronics subsystem comprises architecture for a coordinated scanning mode wherein: the light source subsystem is configured to transmit a first light profile during a first time period, the detector subsystem is configured to scan the array of grouped pixel units in response to the first light profile, the light source subsystem is configured to transmit a second light profile during a second time period, and the detector subsystem is configured to scan the array of grouped pixel units in response to the second light profile.

6. The system of claim 1, wherein the head-mountable interface is configured to establish a brain-computer interface (BCI) and configured to operate in a relay mode to relay light signals generated in response to light emitted from the light sources subsystem and encoding cognitive intents of the user, to the detector subsystem.

7. The system of claim 1, wherein the head-mountable interface includes a cap assembly configured to simultaneously bias the first set of optical fibers and the second set of optical fibers against a scalp region of the user.

8. The system of claim 7, wherein the cap assembly includes a cap substrate retaining an array of ferrules comprising a first subarray of ferrules configured to retain the first set of optical fibers in position and a second subarray of ferrules configured to retain the second set of optical fibers in position.

9. The system of claim 8, wherein the cap assembly is configured to have a stressed configuration, wherein in the stressed configuration, an elastic portion of the cap assembly is stretched, thereby biasing the array of ferrules toward the scalp region of the user.

10. The system of claim 1, wherein the housing is configured to span a parietal lobe and a temporal lobe region of the user during use.

11. A system comprising:
a housing;
a light source subsystem comprising an array of emitters contained within the housing;
a head-mountable interface retained in position by the housing, and physically and optically coupled to the array of emitters by a first set of optical fibers, the head-mountable interface comprising an array of ferrules that, during use of the system, bias ends of the first set of optical fibers against a multidimensional region of interest; and
a detector subsystem contained within the housing and comprising an array of pixels arranged linearly along an axis as a set of grouped pixel units, the set of grouped pixel units optically coupled to the array of ferrules by a second set of optical fibers and configured to receive light signals from the multidimensional region of interest, wherein the set of grouped pixel units omit buffer regions separating adjacent grouped pixel units in the set of grouped pixel units.

12. The system of claim 11, wherein the light source subsystem comprises an array of vertical cavity surface emitting laser (VCSEL) elements.

13. The system of claim 12, wherein each VCSEL element in the array of VCSEL elements is physically separated from other VCSEL elements of the array of VCSEL elements and individually wired to an electronics substrate of the electronics subsystem.

14. The system of claim 12, wherein the array of VCSEL elements is contained within a 4 cm$^2$ footprint.

15. The system of claim 11, wherein the set of grouped pixel units comprise complementary metal oxide semiconductor (CMOS) architecture.

16. The system of claim 11, wherein the head-mountable interface is configured to establish a brain-computer interface (BCI) and operates in a relay mode wherein the head-mountable interface relays light signals, generated in response to light emitted from the light sources subsystem and encoding cognitive intents of the user, to the detector subsystem.

17. The system of claim 11, wherein, during use of the system, the head-mountable interface includes a cap assembly configured to simultaneously bias the first set of optical fibers and the second set of optical fibers against a scalp region of the user.

18. The system of claim 17, wherein the cap assembly includes a cap substrate retaining an array of ferrules configured to retain the first and the second sets of optical fibers in position.

19. The system of claim 17, wherein the cap assembly comprises a stressed configuration, wherein in the stressed configuration, an elastic portion of the cap assembly is stretched, thereby biasing the array of ferrules toward the scalp region of the user.

\* \* \* \* \*